(12) United States Patent
Clark et al.

(10) Patent No.: US 7,319,102 B1
(45) Date of Patent: Jan. 15, 2008

(54) PYRROLO[2,3-D]PYRIMIDINE CYTOKINE INHIBITORS

(75) Inventors: Michael Philip Clark, Maineville, OH (US); Todd Andrew Brugel, West Chester, OH (US); Mark Sabat, Mason, OH (US); Adam Golebiowski, Loveland, OH (US); Roger Gunnard Bookland, Cincinnati, OH (US); Biswanath De, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 483 days.

(21) Appl. No.: 11/005,797

(22) Filed: Dec. 7, 2004

Related U.S. Application Data

(60) Provisional application No. 60/527,967, filed on Dec. 9, 2003.

(51) Int. Cl.
*A61K 31/519* (2006.01)
*C07D 487/04* (2006.01)
*A61P 19/02* (2006.01)

(52) U.S. Cl. .................... 514/265.1; 544/280; 544/230
(58) Field of Classification Search ................ 544/280, 544/230; 514/265.1
See application file for complete search history.

(56) References Cited

FOREIGN PATENT DOCUMENTS

WO         WO 03/074530 A1      9/2003

*Primary Examiner*—Brenda L. Coleman
*Assistant Examiner*—Susanna Moore
(74) *Attorney, Agent, or Firm*—Andrew A. Paul

(57) ABSTRACT

The present invention relates to 2,6,7-substituted pyrrolo[2,3-d]pyrimidines which inhibit the extracellular release of inflammatory cytokines, said cytokines responsible for one or more human or higher mammalian disease states. The present invention further relates to compositions comprising said 2,6,7-substituted pyrrolo[2,3-d]pyrimidines and methods for preventing, abating, or otherwise controlling enzymes which are understood to be the active components responsible for the herein described disease states.

2 Claims, No Drawings

PYRROLO[2,3-D]PYRIMIDINE CYTOKINE INHIBITORS

CROSS REFERENCE TO RELATED APPLICATIONS

This application claims priority under Title 35, United States Code 119(e) from Provisional Application Ser. No. 60/527,967, filed Dec. 9, 2003.

FIELD OF THE INVENTION

The present invention relates to 2,6,7-substituted pyrrolo [2,3-d]pyrimidines which inhibit the extracellular release of inflammatory cytokines, compositions comprising said 2,6,7-substituted pyrrolo[2,3-d]pyrimidines and methods for preventing, abating, or otherwise controlling the extracellular release of inflammatory cytokines.

DETAILED DESCRIPTION OF THE INVENTION

It has been surprisingly found that certain pyrrolo[2,3-d] pyrimidines, inter alia, 2-heterocycloamino-6-[substituted or unsubstituted]acyl-7-[substituted or unsubstituted]aryl pyrrolo[2,3-d]pyrimidines, 2-aryloxy-6-[substituted or unsubstituted]acyl-7-[substituted or unsubstituted]aryl pyrrolo[2,3-d]pyrimidines, or 2-[substituted or unsubstituted] alkylamino-6-[substituted or unsubstituted]acyl-7-[substituted or unsubstituted]aryl pyrrolo[2,3-d]pyrimidines, and derivatives thereof are effective for inhibiting release of inflammatory cytokines, inter alia, interleukin-1 (IL-1) and tumor necrosis factor (TNF) from cells and thereby preventing, abating, or otherwise controlling enzymes which are proposed to be the active components responsible for the herein described disease states.

The present invention relates to pyrrolo[2,3-d]pyrimidines, for example, 2-heterocycloamino-6-[substituted or unsubstituted]acyl-7-[substituted or unsubstituted]aryl pyrrolo[2,3-d]pyrimidines are suitable for mediating, controlling or otherwise inhibiting the extracellular release of certain cytokines, especially inflammatory cytokines, said cytokines playing a role in the stimulation, cause or manifestation of a wide variety of diseases, disease states, or syndromes.

The following chemical hierarchy is used throughout the specification to particularly point out and distinctly claim the units which comprise the compounds of the present invention. The term "hydrocarbyl" stands for any organic molecule, organic functional group, including inorganic atom comprising salts, inter alia, carboxylate salts, quaternary ammonium salts, or for any portion, unit, moiety, and the like, of an organic molecule. Encompassed within the term "hydrocarbyl" are the terms "acyclic" and "cyclic" units which divide hydrocarbyl into cyclic and non-cyclic classes. Acyclic units include alkyl, alkenyl, alkynyl units and their corresponding connecting units, inter alia, alkylene, all of which can be substituted by the suitable substitutions for hydrogen defined herein. Encompassed within the term "cyclic hydrocarbyl" are the carbocyclic, heterocyclic, aryl, and heteroaryl units, and their corresponding connecting units, inter alia, arylene, all of which can be substituted by the suitable substitutions for hydrogen defined herein. Included within the carbocyclic definition are spirocyclic rings, bicyclic rings, and bridged bicyclic rings, as well as fused rings, inter alia, tetralin. For the purposed of the present invention fused ring units which comprise a single heteroatom within a non-aromatic ring, for example, 1,2,3, 4-tetrahydroquinoline having the formula:

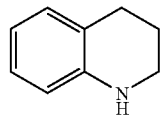

is considered a heterocyclic ring, while 6,7-dihydro-5H-[1] pyridine having the formula:

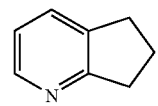

is considered a heteroaryl unit since the heteroatom comprises an aromatic ring.

Included within the definition of "hydrocarbyl" as defined herein above, are the aromatic (aryl) and non-aromatic (carbocyclic) rings, non-limiting examples of which include cyclopropyl, cyclobutanyl, cyclopentanyl, cyclohexanyl, cyclohexenyl, cycloheptanyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl(norboranyl), bicyclo-[0.2.4]-octanyl(caryophyllenyl), spiropentanyl, diclyclopentanespiranyl, decalinyl, phenyl, benzyl, naphthyl, indenyl, 2H-indenyl, azulenyl, phenanthryl, anthryl, fluorenyl, acenaphthylenyl, 1,2,3,4-tetrahydronaphthalenyl, and the like.

Included within the definition of "hydrocarbyl" as defined herein above, are the heteroatom-comprising aromatic (heteroaryl) and non-aromatic (heterocyclic) rings, non-limiting examples of which include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl 2H-indenyl, benzofuranyl, isobenzofuranyl, indolyl, 3H-indolyl, 1H-indolyl, benzoxazolyl, 2H-1-benzopyranyl, quinolinyl, isoquinolinyl, quinazolinyl, 2H-1,4-benzoxazinyl, pyrrolidinyl, pyrrolinyl, quinoxalinyl, furanyl, thiophenyl, benzimidazolyl, and the like each of which can be substituted or unsubstituted.

The term "aryloyl" as it relates to units attached to the core pyrrolo[2,3-d]pyrimidine scaffold further defined herein below. A non limiting example of an aryloyl substituent is a substituted or unsubstituted benzoyl unit having the general formula:

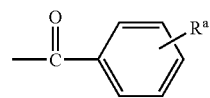

wherein $R^a$ represents one or more possible substitutions for a hydrogen atom.

The term "substituted" is used throughout the specification. The term "substituted" is defined herein as "a hydrocarbyl moiety, whether acyclic or cyclic, which has one or more hydrogen atoms replaced by a substituent or several substituents as defined herein below. The units, which substituted for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidino-propyl is a "substituted $C_3$ alkyl unit," and 2-carboxypyridinyl is a "substituted heteroaryl unit."

The following are non-limiting examples of units which can substitute for hydrogen atoms on a hydrocarbyl or other unit:
  i) —$OR^{12}$;
  ii) —$C(O)R^{12}$
  iii) —$C(O)OR^{12}$
  iv) —$C(O)N(R^{12})_2$;
  v) —CN;
  vi) —$N(R^{12})_2$;
  vii) -halogen; and
  viii) —$CF_3$, —$CCl_3$, —$CBr_3$;

wherein $R^{12}$ is hydrogen, substituted or unsubstituted $C_1$-$C_4$ linear, branched, or cyclic alkyl, and mixtures thereof.

The compounds of the present invention are pyrrolo[2,3-d]pyrimidines having the core scaffold:

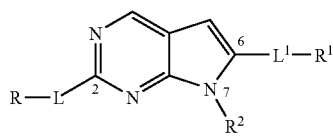

wherein the numbered positions on the ring relate to the naming and substitutions at each position described herein.

R units which comprise the compounds of the present invention are chosen from:
  i) substituted or unsubstituted $C_6$-$C_{10}$ aryl;
  ii) substituted or unsubstituted $C_1$-$C_6$ linear or branched acyclic hydrocarbyl;
  iii) substituted or unsubstituted $C_1$-$C_{10}$ heterocyclic; and
  iv) substituted or unsubstituted $C_1$-$C_{10}$ heteroaryl.

The first aspect of R units relates to substituted or unsubstituted $C_6$-$C_{10}$ aryl units, that is aryl units comprising from 6 to 10 carbon atoms, wherein said substitution is chosen from: halogen, $C_1$-$C_4$ linear or branched alkyl, —OH, —$OR^8$, —CN, —$N(R^8)_2$, —$CO_2R^8$, —$CON(R^8)_2$, —$NR^8COR^8$, and —$NO_2$; each $R^8$ is independently hydrogen, $C_1$-$C_4$ alkyl, or two $R^8$ units can be taken together to form a ring comprising from 3-7 atoms.

The first iteration of this aspect encompasses units chosen from: phenyl, 2-fluorophenyl, 3-fluorophenyl, 4-fluorophenyl, 2,4-difluorophenyl, 3,5-difluorophenyl, 2,6-difluorophenyl, 2-chlorophenyl, 3-chlorophenyl, 4-chlorophenyl, 2,4-dichlorophenyl, 3,5-dichlorophenyl, and 2,6-dichlorophenyl.

A second iteration of this aspect relates to aryl units substituted with a unit chosen from:
  i) —$CO_2R^8$;
  ii) —$CON(R^8)_2$; and
  iii) —$NR^8COR^8$;

wherein $R^8$ is hydrogen, methyl, or ethyl

The third iteration of this aspect relates to aryl units chosen from 2-methylphenyl, 3-methylphenyl, 4-methylphenyl, 2,4-dimethylphenyl, 3,5-dimethylphenyl, 2,6-dimethylphenyl, 2-methoxyphenyl, 3-methoxyphenyl, 4-methoxy-phenyl, 2,4-dimethoxyphenyl, 3,5-dimethoxyphenyl, and 2,6-dimethoxyphenyl.

The second aspect of R units relates to substituted or unsubstituted 5-member ring $C_1$-$C_4$ heterocyclic units, that is heterocyclic units comprising from 1 to 4 carbon atoms. The first iteration of this aspect encompasses units chosen from pyrrolidin-1-yl, pyrrolidin-4-yl, tetrahydrofuran-2-yl, imidazolidin-2-yl, and imidazolidin-4-yl.

The third aspect of R units relates to substituted or unsubstituted 6-member ring $C_1$-$C_5$ heterocyclic units, that is heterocyclic units comprising from 1 to 5 carbon atoms. The first iteration of this aspect encompasses units chosen from piperidin-1-yl, piperidin-4-yl, morpholin-4-yl, and pyran-4-yl.

The fourth aspect of R units relates to substituted or unsubstituted $C_1$-$C_6$ linear or branched alkyl unit having the formula:

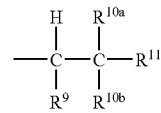

wherein $R^9$, $R^{10a}$, $R^{10b}$, and $R^{11}$ are each independently;
  i) hydrogen;
  ii) $C_1$-$C_4$ alkyl;
  iii) —OH; or
  iv) $C_1$-$C_4$ alkoxy.

A first iteration of this aspect includes chiral R units, for example, units having the formula:

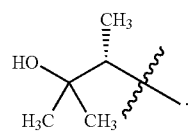

Non-limiting examples of other R units which are encompassed by this iteration include units chosen from 2-methyl-2-hydroxy-1-(S)-methylpropyl, 2-methoxy-1-(S)-methylethyl, 2-methyl-2-cyano-1-(S)-methylpropyl, 2-methyl-2-hydroxy-1-(R)-methylpropyl, 2-methoxy-1-(R)-methylethyl, 2-methyl-2-cyano-1-(R)-methylpropyl, 1-(S)-methylpropyl, and 1-(R)-methylpropyl.

Another iteration includes the racemic mixtures of substituted and unsubstituted $C_1$-$C_6$ alkyl units, for example, units chosen from 1,2-dimethyl-2-hydroxypropyl, 2-methoxy-1-methylethyl, 1,2-dimethyl-2-cyanopropyl, and 1-methylpropyl.

The fifth aspect of R relates to R units which are amino units. The first iteration of this aspect relates to R amino units which are taken together with L units described herein below which comprise a —NH— moiety. Therefore when R and L are taken together they represent hydrazine units, for example, $(CH_3)_2NNH—$, $(CH_3CH_2)_2NNH—$, $C_5H_{10}NNH—$ (piperidin-1-ylamino), and $(C_4H_8ON)NH—$ (morpholin-4-ylamino) as described further herein below.

$R^1$ is chosen from:
  i) hydrogen; and
  ii) substituted or unsubstituted $C_6$-$C_{10}$ aryl.

The first aspect of $R^1$ relates to $C_6$ aryl units chosen from phenyl, 2-chlorphenyl, 4-chlorophenyl, 2,4-dichlorophenyl, 2-fluorophenyl, 4-fluorophenyl, 2,4-difluorophenyl, 2-methylphenyl, 4-methylphenyl, 2,4-dimethylphenyl, and 2,6-dimethylphenyl.

$R^2$ is substituted or unsubstituted $C_6$-$C_{10}$ aryl.

The first aspect of $R^2$ relates to $C_6$ aryl units chosen from phenyl, 2-fluorophenyl, 3-fluorophenyl, 4-fluorophenyl, 2,4-difluorophenyl, 3,5-difluorophenyl, 2,6-difluorophenyl, 2-chlorophenyl, 3-chlorophenyl, 4-chlorophenyl, 2,4-dichlorophenyl, 3,5-dichlorophenyl, and 2,6-dichlorophenyl.

The second aspect of $R^2$ relates to $C_6$ aryl units chosen from 2-methylphenyl, 3-methylphenyl, 4-methylphenyl, 2,4-dimethylphenyl, 3,5-dimethylphenyl, 2,6-dimethylphenyl, 2-methoxyphenyl, 3-methoxyphenyl, 4-methoxy-phenyl, 2,4-dimethoxyphenyl, 3,5-dimethoxyphenyl, and 2,6-dimethoxyphenyl.

L and $L^1$ are linking units each of which independently has the formula:

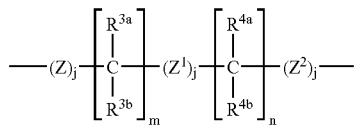

Z, $Z^1$, and $Z^2$ are each independently a unit chosen from:
  i) —$NR^5$—;
  ii) —O—;
  iii) —C(O)—;
  iv) —$CHOR^5$—;
  v) —$SO_2$—;
  vi) —$NR^5SO_2$—; and
  vii) —$SO_2NR^5$—;

each of the indices j is independently 0 or 1. Each $R^5$ unit is independently chosen from:
  i) hydrogen;
  ii) substituted or unsubstituted $C_1$-$C_4$ linear, branched, or cyclic alkyl;
  iii) —$COR^6$;
  iv) —$[C(R^6)_2]_xCO_2R^6$; or
  v) —$[C(R^6)_2]_xCON(R^6)_2$;

$R^6$ is hydrogen, $C_1$-$C_4$ substituted or unsubstituted alkyl, or two $R^6$ units on adjacent carbon atoms can be taken to form a double bond;

$R^{3a}$, $R^{3b}$, $R^{4a}$, and $R^{4b}$ are each independently:
  i) hydrogen;
  ii) —$OR^6$;
  iii) halogen;
  iv) —$[C(R^6)_2]_xCO_2R^6$; or
  v) —$[C(R^6)_2]_xCON(R^6)_2$;
  vi) $C_1$-$C_4$ linear, branched, or cyclic alkyl;
  vii) halogen substituted $C_1$-$C_4$ linear, branched, or cyclic alkyl;
  viii) $C_1$-$C_4$ linear, branched, or cyclic alkoxy;
  ix) $R^{3a}$ and $R^{3b}$ or $R^{4a}$ and $R^{4b}$ can be taken together to form a unit having the formula: C=X wherein X is O, S, $NR^5$, or $NOR^7$; $R^7$ is hydrogen, $C_1$-$C_4$ linear alkyl, and —$COR^6$;
  x) two $R^{3b}$ or two $R^{4b}$ units from adjacent carbon atoms can be taken together to form a double bond;
  xi) $R^{3a}$ and $R^{3b}$ or $R^{4a}$ and $R^{4b}$ can be taken together to form a ring comprising from 3 to 7 atoms; and
  xii) $R^{3a}$ and $R^{3b}$ or $R^{4a}$ and $R^{4b}$ can be taken together to form a unit chosen from =$CH[C(R^6)_2]_xCO_2R^6$, =$CH[C(R^6)_2]_xCON(R^6)_2$, and =$CH[C(R^6)_2]_xOC(O)R^6$;

the indices m and n are each independently from 0 to 5; x is from 0 to 5.

The first aspect of linking groups relates to compounds wherein L and $L^1$ are each independently chosen from:
  i) —NH—;
  ii) —O—;
  iii) —$SO_2$—;
  iv) —C(O)—;
  v) —C=$NOR^6$;
  vi) —$C(R^6)_2$—;
  vii) —$C[=C(R^6)_2]$—; and
  viii) —$C(OR^5)_2$—;

wherein $R^5$ is hydrogen, —$COR^6$, or two $R^5$ units can be taken together with the oxygen atoms to form a cyclic ketal ring comprising 5 or 6 atoms; $R^6$ is methyl, ethyl, or n-propyl.

A second aspect of linking group relates to compound having the formula:

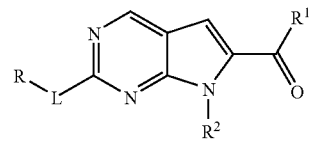

wherein $L^1$ is a carbonyl unit as depicted herein above and L is —NH— or —O—.

Another aspect of linking units relates to $L^1$ units which comprise $R^{3a}$ and $R^{3b}$ or $R^{4a}$ and $R^{4b}$ units which can be taken together to form a unit having the formula: C=X wherein X is $NOR^7$; $R^7$ is hydrogen, $C_1$-$C_4$ linear alkyl, and —$COR^6$.

The first iteration of this aspect relates to units wherein each j unit is equal to 0, the index n is equal to 0, and $R^{3a}$ and $R^{3b}$ are taken together to form an oxime unit having the formula =NOH; compounds of this iteration include compounds having the formula:

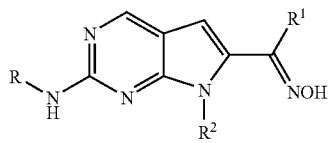

wherein R, $R^1$, and $R^2$ are defined herein above. A further iteration includes compounds wherein the =$NOR^7$ unit comprises an $R^7$ unit which is $C_1$-$C_4$ alkyl, non-limiting examples of which includes [7-(2,6-difluorophenyl)-2-(dimethylamin-1-ylamino)-7H-pyrrolo[2,3-d]pyrimidin-6-yl]-(4-fluorophenyl)-methanone O-methyl-oxime, [7-(2,6-difluorophenyl)-2-(2-hydroxy-1,2-dimethyl-propylamino)-7H-pyrrolo[2,3-d]]pyrimidin-6-yl]-(4-fluorophenyl)-methanone O-methyl-oxime, and (2-chlorophenyl)-[7-(2,6-difluorophenyl)-2-(2-hydroxy-1,2-dimethyl-propylamino)-7H-pyrrolo[2,3-d]pyrimidin-6-yl]-methanone O-methyl-oxime.

Another aspect of $L^1$ units which can be present with any L unit, includes $L^1$ units which are units wherein each j unit is equal to 0, the index n is equal to 0, $R^{3a}$ is hydrogen and $R^{3b}$ is —$OR^6$. The first iteration of this aspect relates to compounds comprising a L units which are —NH— or —O—, and $L^1$ units wherein $R^6$ is hydrogen, for example, compounds having the formula:

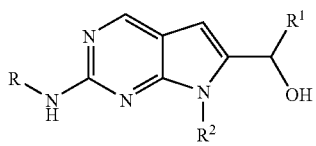

wherein R, $R^1$, and $R^2$ are defined herein above. A further iteration of this aspect relates to $R^6$ units which are acyl, thereby providing $L^1$ having the formula, for example, —CHOC(O)$CH_3$, and providing compounds having, for example, the formula:

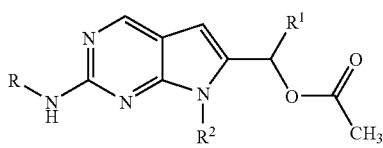

non-limiting examples of which include (2-chlorophenyl)-[7-(2,6-difluorophenyl)-2-(2-hydroxy-1,2-dimethyl-propylamino)-7H-pyrrolo[2,3-d]pyrimidin-6-yl]methylester and 3{7-(2-fluoro-phenyl)-6-[(4-fluorophenyl)-hydroxy-methyl]-7H-pyrrolo[pyrimidin-2-ylamino}-2-methyl-butan-2-ol.

Another aspect of $L^1$ units which can be used in combination with any L unit described herein above, relates to $L^1$ units wherein each index j unit is equal to 0, the index n is equal to 0, and $R^{3a}$ and $R^{3b}$ are taken together to form a ring comprising from 3 to 7 atoms, for example, compounds comprising a cyclic ketal having the formula:

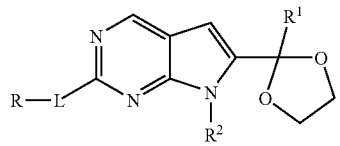

wherein R, $R^1$, and $R^2$ are defined herein above. A non-limiting example of a compound which comprises this aspect of L and $L^1$ includes 3-{7-(2,6-difluorophenyl)-6-[2-(4-fluorophenyl)-[1,3]dioxolan-2-yl]-7H-pyrrolo[2,3-d]pyrimidin-2-ylamino}-2-methyl-butan-2-ol.

Yet another aspect of $L^1$ which can be taken together with any of the L units described herein above, includes $R^{3a}$ and $R^{3b}$ units which are taken together to form a unit having the formula =$CH[C(R^6)_2]_xCO_2R^6$, for example, compounds having the formula:

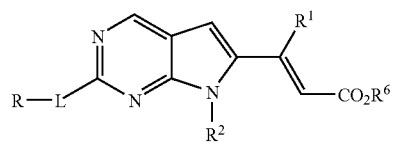

wherein $R^6$ is $C_1$-$C_4$ linear alkyl, R, $R^1$ and $R^2$ are the same as defined herein above.

A further aspect of $L^1$ units relates to compounds comprising a —$SO_2$—$L^1$ unit, for example, compounds having the formula:

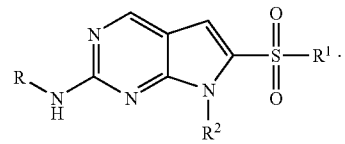

Other examples of $L^1$ units include units having the formula —NHC(O)—, —C(O)$CH_2$—, —C(O)NHC(O)—, —C(O)NH—, and —$CH_2$C(O)—.

The analogs (compounds) of the present invention are arranged into several categories to assist the formulator in applying a rational synthetic strategy for the preparation of analogs which are not expressly exampled herein. The arrangement into categories does not imply increased or decreased efficacy for any of the compositions of matter described herein.

The compounds which comprise Category I of the present invention have the formula:

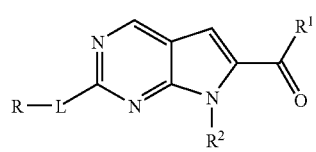

the first aspect of which relates to 2-heterocycloamino-6-[substituted or unsubstituted]acyl-7-[substituted or unsubstituted]aryl pyrrolo[2,3-d]pyrimidines having the formula:

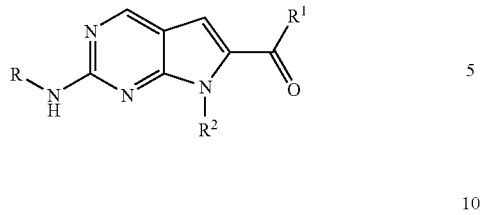

wherein R, $R^1$, and $R^2$ are defined herein below in Table I.

TABLE I

| No. | R | $R^1$ | $R^2$ |
|---|---|---|---|
| 1 | piperidin-1-yl | 2-fluorophenyl | 4-fluorophenyl |
| 2 | piperidin-1-yl | 2-fluorophenyl | 2,6-difluorophenyl |
| 3 | piperidin-1-yl | 4-fluorophenyl | 4-fluorophenyl |
| 4 | piperidin-1-yl | 4-fluorophenyl | 2,6-difluorophenyl |
| 5 | piperidin-1-yl | 2-chlorophenyl | 4-fluorophenyl |
| 6 | piperidin-1-yl | 2-chlorophenyl | 2,6-difluorophenyl |
| 7 | piperidin-1-yl | 2,6-dichlorophenyl | 4-fluorophenyl |
| 8 | piperidin-1-yl | 2,6-dichlorophenyl | 2,6-difluorophenyl |
| 9 | piperidin-1-yl | 2,6-dimethylphenyl | 4-fluorophenyl |
| 10 | piperidin-1-yl | 2,6-dimethylphenyl | 2,6-difluorophenyl |
| 11 | piperazin-1-yl | 2-fluorophenyl | 4-fluorophenyl |
| 12 | piperazin-1-yl | 2-fluorophenyl | 2,6-difluorophenyl |
| 13 | piperazin-1-yl | 4-fluorophenyl | 4-fluorophenyl |
| 14 | piperazin-1-yl | 4-fluorophenyl | 2,6-difluorophenyl |
| 15 | piperazin-1-yl | 2-chlorophenyl | 4-fluorophenyl |
| 16 | piperazin-1-yl | 2-chlorophenyl | 2,6-difluorophenyl |
| 17 | piperazin-1-yl | 2,6-dichlorophenyl | 4-fluorophenyl |
| 18 | piperazin-1-yl | 2,6-dichlorophenyl | 2,6-difluorophenyl |
| 19 | piperazin-1-yl | 2,6-dimethylphenyl | 4-fluorophenyl |
| 20 | piperazin-1-yl | 2,6-dimethylphenyl | 2,6-difluorophenyl |
| 21 | morpholin-4-yl | 2-fluorophenyl | 4-fluorophenyl |
| 22 | morpholin-4-yl | 2-fluorophenyl | 2,6-difluorophenyl |
| 23 | morpholin-4-yl | 4-fluorophenyl | 4-fluorophenyl |
| 24 | morpholin-4-yl | 4-fluorophenyl | 2,6-difluorophenyl |
| 25 | morpholin-4-yl | 2-chlorophenyl | 4-fluorophenyl |
| 26 | morpholin-4-yl | 2-chlorophenyl | 2,6-difluorophenyl |
| 27 | morpholin-4-yl | 2,6-dichlorophenyl | 4-fluorophenyl |
| 28 | morpholin-4-yl | 2,6-dichlorophenyl | 2,6-difluorophenyl |
| 29 | morpholin-4-yl | 2,6-dimethylphenyl | 4-fluorophenyl |
| 30 | morpholin-4-yl | 2,6-dimethylphenyl | 2,6-difluorophenyl |
| 31 | pyran-4-yl | 2-fluorophenyl | 4-fluorophenyl |
| 32 | pyran-4-yl | 2-fluorophenyl | 2,6-difluorophenyl |
| 33 | pyran-4-yl | 4-fluorophenyl | 4-fluorophenyl |
| 34 | pyran-4-yl | 4-fluorophenyl | 2,6-difluorophenyl |
| 35 | pyran-4-yl | 2-chlorophenyl | 4-fluorophenyl |
| 36 | pyran-4-yl | 2-chlorophenyl | 2,6-difluorophenyl |
| 37 | pyran-4-yl | 2,6-dichlorophenyl | 4-fluorophenyl |
| 38 | pyran-4-yl | 2,6-dichlorophenyl | 2,6-difluorophenyl |
| 39 | pyran-4-yl | 2,6-dimethylphenyl | 4-fluorophenyl |
| 40 | pyran-4-yl | 2,6-dimethylphenyl | 2,6-difluorophenyl |

The compounds which comprise the first aspect of Category I of the present invention can be prepared by the procedure outlined herein below in Scheme I.

Scheme I

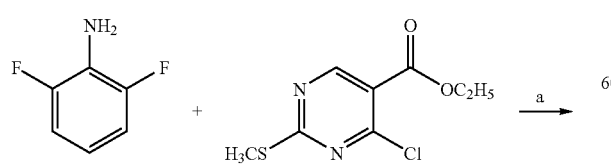

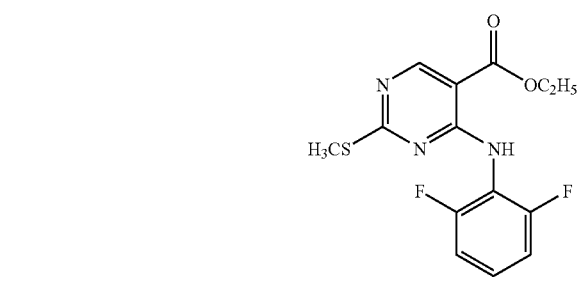

Reagents and conditions: (a) $CH_3CN$; 90° C., 4 hr.

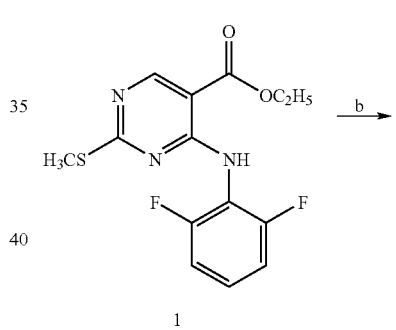

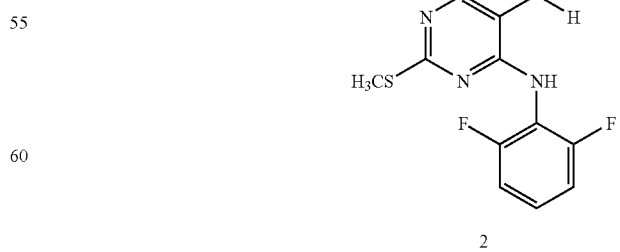

Reagents and conditions: (b) (i) LAH, THF; 0° C.-rt, 17 hr (ii) $MnO_2$, $CH_2Cl_2$; rt, 17 hr.

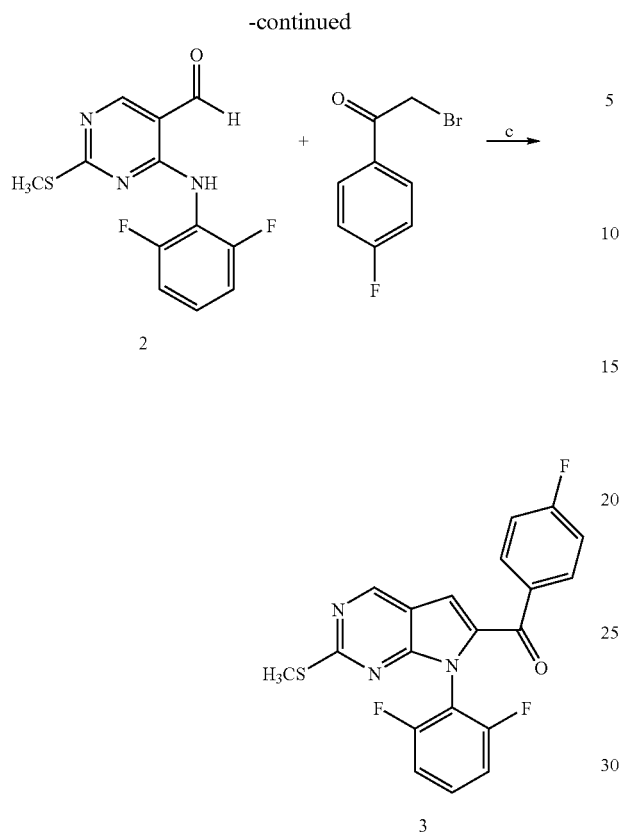

Reagents and condtions: (c) K₂CO₃, DMF; rt, 18 hr.

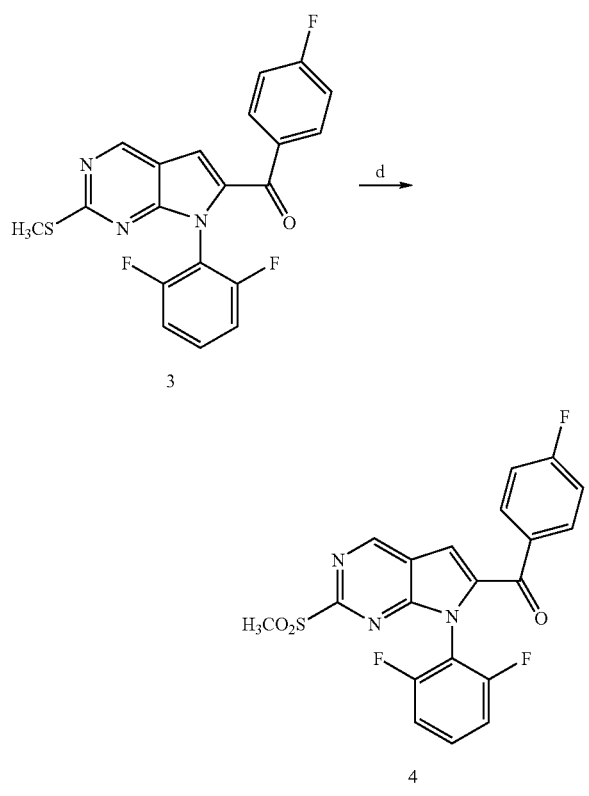

Reagents and condtions: (d) Oxone, H₂O; rt, 1 hr.

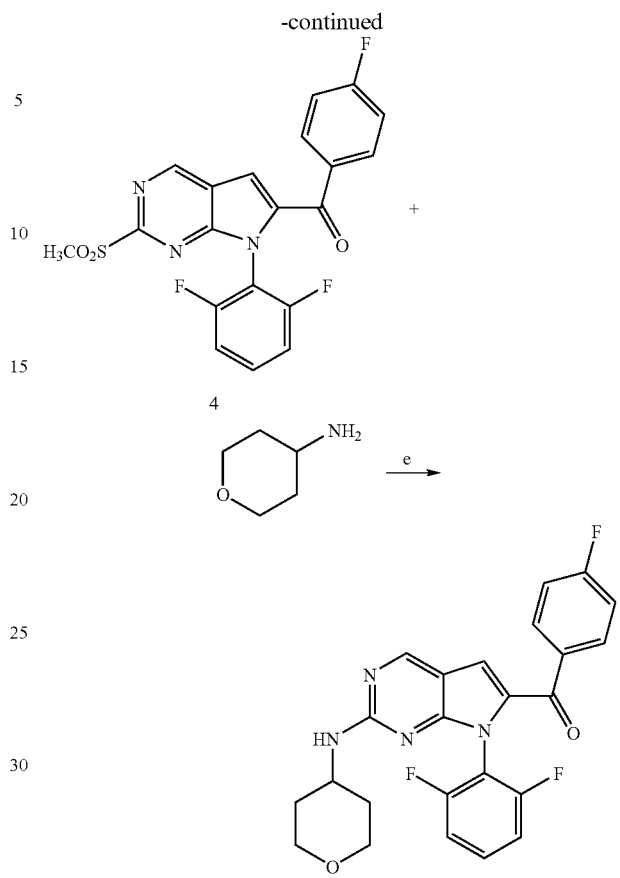

Reagents and conditions: (e) NMP; 90° C., 19 hr.

EXAMPLE 1

[7-(2,6-Difluorophenyl)-2-(tetrahydro-pyran-4-ylamino)-7H-pyrrolo[2,3-d]pyrimidin-6-yl]-(4-fluorophenyl)-methanone (5)

Preparation of 4-(2,6-difluoro-phenylamino)-2-methylsulfanyl-pyrimidine-5-carboxylic acid ethyl ester (1): To a solution of 4-chloro-2-methylsulfanyl-pyrimidine-5-carboxylic acid ethyl ester (10.0 g, 43.1 mmol) in acetonitrile (107 mL) is added 2,6-difluoroaniline (9.3 mL, 86.2 mmol). The mixture is heated to 90° C. for 4 hours. The reaction is cooled to room temperature and stored at 0° C. for 15 hours. The white precipitate which forms is filtered and washed with 20% EtOAc/hexanes to afford 14.3 g of the desired product which is used without further purification: $^1$H NMR (300 MHz, CDCl$_3$/MeOH) δ 9.70 (s, 1H), 8.20 (s, 1H), 7.82 (s, 2H), 5.23 (s, 2H), 3.18 (s, 3H), 2.25 (s, 3H); ESI$^+$ MS: m/z (rel intensity) 326.0 (100, M$^+$+H).

Preparation of 4-(2,6-difluoro-phenylamino)-2-methylsulfanyl-pyrimidine-5-carbaldehyde (2): To a cold (0° C.) solution of lithium aluminum hydride (145.0 mL of 1M solution in THF, 145.0 mmol) in THF (1.0 L) is added portion-wise 4-(2,6-difluoro-phenylamino)-2-methylsulfanyl-pyrimidine-5-carboxylic acid ethyl ester, 1, (43.0 g, 132.0 mmol). The reaction is allowed to warm to room temp and stirred for an additional 17 hours. The reaction is then re-cooled to 0° C., and $H_2O$ (17 mL) added dropwise to the mixture. After stirring 30 minutes at room temperature, NaOH solution (17 mL of 2N solution) is added followed by $H_2O$ (23 mL). The resulting suspension is filtered through celite and washed thoroughly with EtOAc. The filtrate is concentrated in vacuo to afford 28.4 g of the intermediate alcohol, which is used without further purification: $^1H$ NMR (300 MHz, $CH_3OD$) δ 8.02 (s, 1H), 7.26-7.24 (m, 1H), 7.08 (t, J=8.1 Hz, 2H), 4.90 (s, 2H), 2.20 (s, 3H); $ESI^+$ MS: m/z (rel intensity) 284.1 (100, $M^++H$).

To a solution of the intermediate alcohol (14.4 g, 50.9 mmol) in $CH_2Cl_2$ (120 mL) is charged manganese (IV) oxide (44.4 g, 509.0 mmol). After stirring the suspension at room temperature for 17 hours, the mixture is filtered through celite, and washed with $CH_2Cl_2$. The filtrate is concentrated in vacuo to afford 14.0 g of the desired product as yellow solid: $^1H$ NMR (300 MHz, $CDCl_3$) δ 9.95 (s, 1H), 8.58 (s, 1H), 7.40-6.98 (m, 3H), 2.40 (s, 3H); $ESI^+$ MS: m/z (rel intensity) 281.9 (100, $M^++H$).

Preparation of [7-(2,6-difluorophenyl)-2-methylsulfanyl-7H-pyrrolo[2,3-d]pyrimidin-6-yl]-(4-fluorophenyl)-methanone (3): To a solution of 4-(2,6-difluoro-phenylamino)-2-methylsulfanyl-pyrimidine-5-carbaldehyde, 2, (5.4 g, 8.3 mmol) in DMF (107 mL) is added 2-bromo-1-(2-fluorophenyl)-ethanone (2.7 g, 12.5 mmol) and potassium carbonate (8.0 g, 57.7 mmol). The reaction mixture is stirred at room temp for 18 hours then diluted with EtOAc and washed with aqueous saturated $NH_4Cl$ three times. The organic phase is washed with aqueous saturated $NaHCO_3$ and brine, dried ($MgSO_4$), filtered and concentrated in vacuo. The resulting residue is purified over silica (10% EtOAc//hexanes) to afford 4.6 g of the desired product as a purple solid: $^1H$ NMR (300 MHz, $CDCl_3$) δ 8.98 (s, 1H), 8.00 (dd, J=5.4, 3.4 Hz, 2H), 7.50-7.40 (m, 1H), 7.25-7.05 (m, 5H), 2.52 (s, 3H); $ESI^+$ MS: m/z (rel intensity) 400.1 (100, $M^++H$).

Preparation of [7-(2,6-difluorophenyl)-2-methanesulfonyl-7H-pyrrolo[2,3-d]pyrimidin-6-yl]-(4-fluorophenyl)-methanone (4): To a solution of [7-(2,6-difluoro-phenyl)-2-methylsulfanyl-7H-pyrrolo[2,3-d]pyrimidin-6-yl]-(4-fluoro-phenyl)-methanone, 3, (4.6 g, 11.5 mmol) in THF:methanol (108 mL of 1:1 mixture) is added dropwise a solution of Oxone® (potassium peroxymonosulfate) (28.4 g, 46.1 mmol) in $H_2O$ (83 mL). After stirring the reaction for 1 hour at room temperature, the solution is poured into aqueous saturated $NaHCO_3$. The aqueous phase is extracted three times with EtOAc and the combined organic phases are dried ($MgSO_4$), filtered and concentrated in vacuo to afford 4.5 g of the desired product which is used without further purification.

Preparation of [7-(2,6-difluorophenyl)-2-(tetrahydropyran-4-ylamino)-7H-pyrrolo[2,3-d]pyrimidin-6-yl]-(4-fluorophenyl)-methanone (5): To a solution of [7-(2,6-difluoro-phenyl)-2-methanesulfonyl-7H-pyrrolo[2,3-d]pyrimidin-6-yl]-(4-fluoro-phenyl)-methanone, 4, (0.50 g, 1.28 mmol) in 1-methyl-2-pyrrolidinone (4 mL) is added 4-aminotetrahydropyran (0.18 g, 1.80 mmol). The reaction mixture is heated to 90° C. for 19 hours after which the reaction is cooled to room temperature and concentrated in vacuo. The crude residue is purified over silica (40% EtOAc/hexanes) to afford 444 mg of the desired product as a yellow solid: $^1H$ NMR (300 MHz, $CDCl_3$) δ 8.74 (s, 1H), 7.93 (dd, J=9.0, 5.4 Hz, 2H), 7.48-7.39 (m, 1H), 7.20 (t, J=9.0 Hz, 2H), 7.12-7.06 (m, 3H), 4.10-3.95 (m, 3H), 3.49 (t, J=7.6 Hz, 2H), 2.40 (t, J=7.6 Hz, 2H), 2.06-2.01 (m, 2H); HRMS calcd for $C_{24}H_{19}F_3N_4O_2$ $(M+H)^+$ 453.1539; found 453.1551.

(2-Chlorophenyl)-[7-(2,6-difluorophenyl)-2-(piperidin-1-ylamino)-7H-pyrrolo[2,3-d]pyrimidin-6-yl]-methanone: $^1H$ NMR (300 MHz, $CDCl_3$) δ 8.83 (s, 1H), 7.53-7.33 (m, 5H), 7.10 (t, J=7.7 Hz, 2H), 6.89 (s, 1H), 2.86-2.76 (m, 4H), 1.76 (dddd, J=5.4, 5.4, 5.4, 5.4 Hz, 4H), 1.48-1.38 (m, 2H). HRMS calcd for $C_{24}H_{21}ClF_2N_5O$ $(M+H)^+$ 468.1403; found 468.1407.

(2-Chlorophenyl)-[7-(2,6-difluorophenyl)-2-(4-methyl-piperazin-1-ylamino)-7H-pyrrolo[2,3-d]pyrimidin-6-yl]-methanone: $^1H$ NMR (300 MHz, $CDCl_3$) δ 8.86 (s, 1H), 7.53-7.35 (m, 5H), 6.92 (s, 1H), 7.12 (t, J=7.8 Hz, 2H), 2.95 (bd m, 4H), 2.70 (bd m, 4H), 2.39 (s, 3H). HRMS calcd for $C_{24}H_{22}ClF_2N_6O$ $(M+H)^+$ 483.1512; found 483.1509.

(2-Chlorophenyl)-[7-(2,6-difluorophenyl)-2-(morpholin-4-ylamino)-7H-pyrrolo[2,3-d]pyrimidin-6-yl]-methanone: $^1H$ NMR (300 MHz, $CDCl_3$) δ 8.86 (s, 1H), 7.53-7.37 (m, 5H), 7.10 (dd, J=8.4, 7.7 Hz, 2H), 6.92 (s, 1H), 6.14 (bd s, NH), 3.88 (t, J=4.5 Hz, 4H), 2.93 (t, J=4.5 Hz, 4H). HRMS calcd for $C_{23}H_{19}ClF_2N_5O_2$ $(M+H)^+$ 470.1195; found 470.1187.

[7-(2,6-Difluorophenyl)-2-(4-methyl-piperazin-1-ylamino)-7H-pyrrolo[2,3-d]pyrimidin-6-yl]-(4-fluorophenyl)-methanone: $^1H$ NMR (300 MHz, $CDCl_3$) δ 8.90 (s, 1H), 7.96-7.91 (m, 2H), 7.50-7.41 (m, 1H), 7.29-7.06 (m, 6H), 6.00 (s, 1H), 3.11-3.02 (m, 4H), 2.85-2.75 (m, 4H), 2.43 (s, 3H); $ESI^+$ MS: m/z (rel intensity) 467.0 (100, $M^++H$).

(4-Fluorophenyl)-[7-(4-fluorophenyl)-2-(tetrahydropyran-4-ylamino)-7H-pyrrolo[2,3-d]pyrimidin-6-yl]-methanone: $^1H$ NMR (300 MHz, $CDCl_3$) δ 8.75 (s, 1H), 7.96 (dd, J=8.7, 5.4 Hz, 2H), 7.38 (dd, J=9.0, 5.1 Hz, 2H), 7.23-7.15 (m, 4H), 7.03 (s, 1H), 4.05-3.94 (m, 3H), 3.52 (t, J=10.5 Hz, 2H), 2.06-1.97 (m, 2H), 1.64-1.50 (m, 2H). HRMS calcd for $C_{24}H_{21}F_2N_4O_2$ $(M+H)^+$ 435.1633; found 435.1626.

(2-Chlorophenyl)-[7-(4-fluorophenyl)-2-(tetrahydropyran-4-ylamino)-7H-pyrrolo[2,3-d]pyrimidin-6-yl]-methanone: $^1H$ NMR (300 MHz, $CDCl_3$) δ 8.68 (s, 1H), 7.55-7.36 (m, 6H), 7.20 (ddd, J=9.0, 9.0, 1.5 Hz, 2H), 6.85 (s, 1H), 4.01-3.97 (m, 3H), 3.51 (t, J=11.4 Hz, 2H), 2.06-1.97 (m, 2H), 1.56 (ddd, J=23.7, 11.4, 4.2 Hz, 2H). HRMS calcd for $C_{24}H_{21}ClFN_4O_2$ $(M+H)^+$ 451.1337; found 451.1328.

(2,4-Dimethylphenyl)-[7-(4-fluorophenyl)-2-(tetrahydropyran-4-ylamino)-7H-pyrrolo[2,3-d]pyrimidin-6-yl]-methanone: $^1H$ NMR (300 MHz, $CDCl_3$) δ 8.67 (s, 1H), 7.50 (d, J=7.7 Hz, 2H), 7.39 (dd, J=9.0, 4.8 Hz, 2H), 7.17 (t, J=8.4 Hz, 2H), 7.14-7.06 (m, 2H), 6.82 (s, 1H), 5.32 (bd s, NH), 4.06-3.94 (m, 3H), 3.52 (ddd, J=15.6, 15.6, 1.8 Hz, 2H), 2.41 (s, 3H), 2.39 (s, 3H), 2.08-2.00 (m, 2H), 1.64-1.51 (m, 2H). HRMS calcd for $C_{26}H_{26}FN_4O_2$ $(M+H)^+$ 445.2040; found 445.2031.

The second aspect of Category I relates to 2-aryloxy-6-[substituted or unsubstituted]acyl-7-[substituted or unsubstituted]aryl pyrrolo[2,3-d]pyrimidines having the formula:

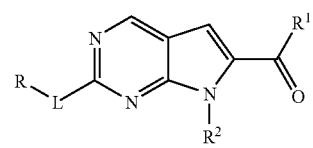

wherein L, R, $R^1$, and $R^2$ are defined herein below in Table II.

TABLE II

| No. | L    | R                 | R¹                  | R²                  |
|-----|------|-------------------|---------------------|---------------------|
| 41  | —O—  | phenyl            | 2-fluorophenyl      | 4-fluorophenyl      |
| 42  | —O—  | phenyl            | 2-fluorophenyl      | 2,6-difluorophenyl  |
| 43  | —O—  | phenyl            | 4-fluorophenyl      | 4-fluorophenyl      |
| 44  | —O—  | phenyl            | 4-fluorophenyl      | 2,6-difluorophenyl  |
| 45  | —O—  | phenyl            | 2-chlorophenyl      | 4-fluorophenyl      |
| 46  | —O—  | phenyl            | 2-chlorophenyl      | 2,6-difluorophenyl  |
| 47  | —O—  | phenyl            | 2,6-dichlorophenyl  | 4-fluorophenyl      |
| 48  | —O—  | phenyl            | 2,6-dichlorophenyl  | 2,6-difluorophenyl  |
| 49  | —O—  | phenyl            | 2,6-dimethylphenyl  | 4-fluorophenyl      |
| 50  | —O—  | phenyl            | 2,6-dimethylphenyl  | 2,6-difluorophenyl  |
| 51  | —NH— | phenyl            | 2-fluorophenyl      | 4-fluorophenyl      |
| 52  | —NH— | phenyl            | 2-fluorophenyl      | 2,6-difluorophenyl  |
| 53  | —NH— | phenyl            | 4-fluorophenyl      | 4-fluorophenyl      |
| 54  | —NH— | phenyl            | 4-fluorophenyl      | 2,6-difluorophenyl  |
| 55  | —NH— | phenyl            | 2-chlorophenyl      | 4-fluorophenyl      |
| 56  | —NH— | phenyl            | 2-chlorophenyl      | 2,6-difluorophenyl  |
| 57  | —NH— | phenyl            | 2,6-dichlorophenyl  | 4-fluorophenyl      |
| 58  | —NH— | phenyl            | 2,6-dichlorophenyl  | 2,6-difluorophenyl  |
| 59  | —NH— | phenyl            | 2,6-dimethylphenyl  | 4-fluorophenyl      |
| 60  | —NH— | phenyl            | 2,6-dimethylphenyl  | 2,6-difluorophenyl  |
| 61  | —O—  | 2,6-difluorophenyl| 2-fluorophenyl      | 4-fluorophenyl      |
| 62  | —O—  | 2,6-difluorophenyl| 2-fluorophenyl      | 2,6-difluorophenyl  |
| 63  | —O—  | 2,6-difluorophenyl| 4-fluorophenyl      | 4-fluorophenyl      |
| 64  | —O—  | 2,6-difluorophenyl| 4-fluorophenyl      | 2,6-difluorophenyl  |
| 65  | —O—  | 2,6-difluorophenyl| 2-chlorophenyl      | 4-fluorophenyl      |
| 66  | —O—  | 2,6-difluorophenyl| 2-chlorophenyl      | 2,6-difluorophenyl  |
| 67  | —O—  | 2,6-difluorophenyl| 2,6-dichlorophenyl  | 4-fluorophenyl      |
| 68  | —O—  | 2,6-difluorophenyl| 2,6-dichlorophenyl  | 2,6-difluorophenyl  |
| 69  | —O—  | 2,6-difluorophenyl| 2,6-dimethylphenyl  | 4-fluorophenyl      |
| 70  | —O—  | 2,6-difluorophenyl| 2,6-dimethylphenyl  | 2,6-difluorophenyl  |
| 71  | —NH— | 2,6-difluorophenyl| 2-fluorophenyl      | 4-fluorophenyl      |
| 72  | —NH— | 2,6-difluorophenyl| 2-fluorophenyl      | 2,6-difluorophenyl  |
| 73  | —NH— | 2,6-difluorophenyl| 4-fluorophenyl      | 4-fluorophenyl      |
| 74  | —NH— | 2,6-difluorophenyl| 4-fluorophenyl      | 2,6-difluorophenyl  |
| 75  | —NH— | 2,6-difluorophenyl| 2-chlorophenyl      | 4-fluorophenyl      |
| 76  | —NH— | 2,6-difluorophenyl| 2-chlorophenyl      | 2,6-difluorophenyl  |
| 77  | —NH— | 2,6-difluorophenyl| 2,6-dichlorophenyl  | 4-fluorophenyl      |
| 78  | —NH— | 2,6-difluorophenyl| 2,6-dichlorophenyl  | 2,6-difluorophenyl  |
| 79  | —NH— | 2,6-difluorophenyl| 2,6-dimethylphenyl  | 4-fluorophenyl      |
| 80  | —NH— | 2,6-difluorophenyl| 2,6-dimethylphenyl  | 2,6-difluorophenyl  |

The following are non-limiting examples of the second aspect of Category II according to the present invention.

(2-Chlorophenyl)-[2-(2,6-difluorophenoxy)-7-(2,6-difluoro-phenyl)-7H-pyrrolo[2,3-d]pyrimidin-6-yl]-methanone: ¹H NMR (300 MHz, CDCl₃) δ 8.91 (s, 1H), 7.55-7.36 (m, 6H), 7.24-6.98 (m, 6H). HRMS calcd for $C_{25}H_{13}ClF_4N_3O_2$ (M+H)⁺ 498.0632; found 498.0616.

(2-Chlorophenyl)-[7-(2,6-difluorophenyl)-2-phenoxy-7H-pyrrolo[2,3-d]pyrimidin-6-yl]-methanone: ¹H NMR (300 MHz, CDCl₃) δ 8.92 (s, 1H), 7.55-7.40 (m, 5H), 7.27-7.23 (m, 4H), 7.11 (t, J=8.4 Hz, 2H), 7.05 (s, 1H). HRMS calcd for $C_{25}H_{15}ClF_2N_3O_2$ (M+H)⁺ 462.0821; found 462.0830.

[7-(2,6-Difluorophenyl)-2-(2,6-difluorophenylamino)-7H-pyrrolo[2,3-d]pyrimidin-6-yl]-(4-fluorophenyl)-methanone: ¹H NMR (300 MHz, CDCl₃) δ 8.78 (s, 1H), 7.87 (dd, J=8.7, 5.4 Hz, 2H), 7.41-7.32 (m, 1H), 7.19-7.09 (m, 4H), 7.00 (t, J=8.1 Hz, 2H), 6.89 (t, J=8.1 Hz, 2H). HRMS calcd for $C_{25}H_{14}F_5N_4O$ (M+H)⁺ 481.1088; found 481.1100.

[7-(2,6-Difluorophenyl)-2-phenoxy-7H-pyrrolo[2,3-d]pyrimidin-6-yl]-(4-fluorophenyl)-methanone: ¹H NMR (300 MHz, CDCl₃) δ 8.98 (s, 1H), 7.98 (dd, J=6.6, 5.5 Hz, 2H), 7.47-7.30 (m, 3H), 7.29-7.20 (m, 6H), 7.09 (t, J=8.1 Hz, 2H), HRMS calcd for $C_{25}H_{14}F_3N_3O_2$ (M+H)⁺ 446.1116; found 446.1114.

[2-(2,6-Difluorophenylamino)-7-(2-fluorophenyl)-7H-pyrrolo[2,3-d]pyrimidin-6-yl]-(4-fluoro-phenyl)-methanone: ¹H NMR (300 MHz, CDCl₃) δ 8.84 (s, 1H), 7.98 (dd, J=5.5, 3.1 Hz, 2H), 7.65 (t, J=7.5, 1H), 7.41-6.90 (m, 8H), 4.15 (dd, J=14.1, 7.1 Hz, 1H); HRMS calcd for $C_{25}H_{14}F_4N_4O$ (M+H)⁺ 463.1182; found 463.1204.

(4-Fluorophenyl)-[7-(4-fluorophenyl)-2-(1-phenyl-ethylamino)-7H-pyrrolo[2,3-d]pyrimidin-6-yl]-methanone: ¹H NMR (300 MHz, CDCl₃) δ 8.69 (s, 1H), 7.93 (dd, J=5.5, 3.3 Hz, 2H), 7.35-7.10 (m, 11H), 6.98 (s, 1H), 5.82 (br s, 1H), 4.90 (br s, 1H), 1.55 (d, J=6.8 Hz, 3H); HRMS calcd for $C_{27}H_{20}F_2N_4O$ (M+H)⁺ 455.1683, found 455.1670.

(2-Chlorophenyl)-[7-(4-fluorophenyl)-2-(1-phenyl-ethylamino)-7H-pyrrolo[2,3-d]pyrimidin-6-yl]-methanone: ¹H NMR (300 MHz, CDCl₃) δ 8.64 (s, 1H), 7.47-7.10 (m, 13H), 6.81 (s, 1H), 5.95 (br s, 1H), 5.00 (br s, 1H), 1.55 (d, J=6.8 Hz, 3H); HRMS calcd for $C_{27}H_{20}ClFN_4O$ (M+H)⁺ 471.1388, found 471.1382.

The third aspect of Category I relates to 2-[substituted or unsubstituted]alkylamino-6-[substituted or unsubstituted]acyl-7-[substituted or unsubstituted]aryl pyrrolo[2,3-d]pyrimidines having the formula:

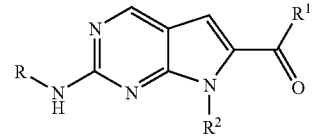

wherein R, R¹, and R² are defined herein below in Table III.

TABLE III

| No. | R                                  | R¹             | R²             |
|-----|------------------------------------|----------------|----------------|
| 81  | 2-methyl-2-hydroxy-1-(S)-methylpropyl | 4-fluorophenyl | 4-fluorophenyl |
| 82  | 2-methoxy-1-(S)-methylethyl        | 4-fluorophenyl | 4-fluorophenyl |
| 83  | 2-methyl-2-cyano-1-(S)-methylpropyl | 4-fluorophenyl | 4-fluorophenyl |
| 84  | 2-methyl-2-hydroxy-1-(R)-methylpropyl | 4-fluorophenyl | 4-fluorophenyl |
| 85  | 2-methoxy-1-(R)-methylethyl        | 4-fluorophenyl | 4-fluorophenyl |
| 86  | 2-methyl-2-cyano-1-(R)-methylpropyl | 4-fluorophenyl | 4-fluorophenyl |

TABLE III-continued

| No. | R | R$^1$ | R$^2$ |
|---|---|---|---|
| 87 | 1-(S)-methylpropyl | 4-fluorophenyl | 4-fluorophenyl |
| 88 | 1-(R)-methylpropyl | 4-fluorophenyl | 4-fluorophenyl |
| 89 | N,N-dimethylamino | 4-fluorophenyl | 4-fluorophenyl |
| 90 | N,N-diethylamino | 4-fluorophenyl | 4-fluorophenyl |
| 91 | 2-methyl-2-hydroxy-1-(S)-methylpropyl | 4-fluorophenyl | 2,6-difluorophenyl |
| 92 | 2-methoxy-1-(S)-methylethyl | 4-fluorophenyl | 2,6-difluorophenyl |
| 93 | 2-methyl-2-cyano-1-(S)-methylpropyl | 4-fluorophenyl | 2,6-difluorophenyl |
| 94 | 2-methyl-2-hydroxy-1-(R)-methylpropyl | 4-fluorophenyl | 2,6-difluorophenyl |
| 95 | 2-methoxy-1-(R)-methylethyl | 4-fluorophenyl | 2,6-difluorophenyl |
| 96 | 2-methyl-2-cyano-1-(R)-methylpropyl | 4-fluorophenyl | 2,6-difluorophenyl |
| 97 | 1-(S)-methylpropyl | 4-fluorophenyl | 2,6-difluorophenyl |
| 98 | 1-(R)-methylpropyl | 4-fluorophenyl | 2,6-difluorophenyl |
| 99 | N,N-dimethylamino | 4-fluorophenyl | 2,6-difluorophenyl |
| 100 | N,N-diethylamino | 4-fluorophenyl | 2,6-difluorophenyl |
| 101 | 2-methyl-2-hydroxy-1-(S)-methylpropyl | 2-chlorophenyl | 4-fluorophenyl |
| 102 | 2-methoxy-1-(S)-methylethyl | 2-chlorophenyl | 4-fluorophenyl |
| 103 | 2-methyl-2-cyano-1-(S)-methylpropyl | 2-chlorophenyl | 4-fluorophenyl |
| 104 | 2-methyl-2-hydroxy-1-(R)-methylpropyl | 2-chlorophenyl | 4-fluorophenyl |
| 105 | 2-methoxy-1-(R)-methylethyl | 2-chlorophenyl | 4-fluorophenyl |
| 106 | 2-methyl-2-cyano-1-(R)-methylpropyl | 2-chlorophenyl | 4-fluorophenyl |
| 107 | 1-(S)-methylpropyl | 2-chlorophenyl | 4-fluorophenyl |
| 108 | 1-(R)-methylpropyl | 2-chlorophenyl | 4-fluorophenyl |
| 109 | N,N-dimethylamino | 2-chlorophenyl | 4-fluorophenyl |
| 110 | N,N-diethylamino | 2-chlorophenyl | 4-fluorophenyl |
| 111 | 2-methyl-2-hydroxy-1-(S)-methylpropyl | 2-chlorophenyl | 4-fluorophenyl |
| 112 | 2-methoxy-1-(S)-methylethyl | 2-chlorophenyl | 2,6-difluorophenyl |
| 113 | 2-methyl-2-cyano-1-(S)-methylpropyl | 2-chlorophenyl | 2,6-difluorophenyl |
| 114 | 2-methyl-2-hydroxy-1-(R)-methylpropyl | 2-chlorophenyl | 2,6-difluorophenyl |
| 115 | 2-methoxy-1-(R)-methylethyl | 2-chlorophenyl | 2,6-difluorophenyl |
| 116 | 2-methyl-2-cyano-1-(R)-methylpropyl | 2-chlorophenyl | 2,6-difluorophenyl |
| 117 | 1-(S)-methylpropyl | 2-chlorophenyl | 2,6-difluorophenyl |
| 118 | 1-(R)-methylpropyl | 2-chlorophenyl | 2,6-difluorophenyl |
| 119 | N,N-dimethylamino | 2-chlorophenyl | 2,6-difluorophenyl |
| 120 | N,N-diethylamino | 2-chlorophenyl | 2,6-difluorophenyl |

The following are non-limiting examples of the third aspect of Category I.

N,N-Dimethyl-N'-[7-(2,6-difluoro-phenyl)-7H-pyrrolo[2,3-d]pyrimidin-6-yl]-2-hydrazino-(4-fluoro-phenyl)-methanone: $^1$H NMR (300 MHz, CDCl$_3$) δ 8.90 (s, 1H), 7.92 (dd, J=8.8, 5.5 Hz, 2H), 7.50-7.39 (m, 1H), 7.20 (t, J=8.7 Hz, 2H), 7.10 (t, J=8.7 Hz, 2H), 7.09 (s, 1H), 6.01 (bd s, NH), 2.70 (s, 6H); HRMS calcd for C$_{21}$H$_{16}$F$_3$N$_5$O (M+H)$^+$ 412.1385; found 412.1390.

N,N-Dimethyl-N'-(2-chlorophenyl)-[7-(2,6-difluoro-phenyl)-7H-pyrrolo[2,3-d]pyrimidin-6-yl]-2-hydrazino-methanone: $^1$H NMR (300 MHz, CDCl$_3$) δ 8.88 (s, 1H), 7.59-7.32 (m, 5H), 7.17 (t, J=8.4 Hz, 2H), 6.95 (s, 1H), 2.72 (s, 6H). HRMS calcd for C$_{21}$H$_{17}$ClF$_2$N$_5$O (M+H)$^+$ 468.1403; found 468.1407.

(S)-(2-Chloro-phenyl)-[7-(2,6-difluoro-phenyl)-2-(2-hydroxy-1,2-dimethyl-propylamino)-7H-pyrrolo[2,3-d]pyrimidin-6-yl]-methanone: $^1$H NMR (300 MHz, CDCl$_3$) δ 8.64 (s, 1H), 7.58-7.11 (m, 7H), 6.92 (s, 1H), 4.03 (m, 1H), 1.27 (s, 9H). HRMS calcd for C$_{24}$H$_{21}$ClF$_2$N$_4$O$_2$ (M+H)$^+$ 471.1399; found 471.1405.

(S)-[2-sec-Butylamino-7-(2,6-difluoro-phenyl)-7H-pyrrolo[2,3-d]pyrimidin-6-yl]-(2-chloro-phenyl)-methanone: $^1$H NMR (300 MHz, CDCl$_3$) δ 8.64 (s, 1H), 7.52-7.34 (m, 5H), 7.11 (t, J=8.1 Hz, 2H), 6.88 (s, 1H), 5.42 (bd s, NH), 3.94 (m, 1H), 1.65-1.46 (m, 2H), 1.18 (d, J=6.4 Hz, 3H), 0.92 (t, J=7.3 Hz, 3H). HRMS calcd for C$_{23}$H$_{20}$ClF$_2$N$_4$O (M+H)$^+$ 441.1294; found 441.1276.

(S)-[7-(2,6-Difluoro-phenyl)-2-(2-hydroxy-1,2-dimethyl-propylamino)-7H-pyrrolo[2,3-d]pyrimidin-6-yl]-(4-fluoro-phenyl)-methanone: $^1$H NMR (300 MHz, CDCl$_3$) δ 8.67 (s, 1H), 7.86 (dd, J=8.4, 5.1 Hz, 2H), 7.46-7.36 (m, 1H), 7.15 (t, J=8.4 Hz, 2H), 7.09-7.03 (m, 3H), 4.00 (bd m, 1H), 1.17 (d, J=7.2 Hz, 3H), 1.16 (s, 6H). HRMS calcd for C$_{24}$H$_{22}$F$_5$N$_4$O$_2$ (M+H)$^+$ 455.1695; found 455.1716.

(2-Chloro-phenyl)-[7-(2,6-difluoro-phenyl)-2-methoxyamino-7H-pyrrolo[2,3-d]pyrimidin-6-yl]-methanone: $^1$H NMR (300 MHz, CDCl$_3$) δ 8.88 (s, 1H), 7.94 (s, 1H), 7.54-7.36 (m, 4H), 7.30 (s, 1H), 7.12 (t, J=8.2 Hz, 2H) 6.98 (s, 1H), 3.88 (s, 3H): HRMS calcd for C$_{20}$H$_{13}$ClF$_2$N$_4$O$_2$ (M+H)$^+$ 415.0773; found 415.0755.

(S)-(4-Fluoro-phenyl)-[7-(2-fluoro-phenyl)-2-(2-hydroxy-1,2-dimethyl-propylamino)-7H-pyrrolo[2,3-d]pyrimidin-6-yl]-methanone: $^1$H NMR (300 MHz, CDCl$_3$) δ 8.72 (s, 1H), 7.96-7.92 (m, 2H), 7.60-7.52 (m, 1H), 7.47-7.41 (m, 1H), 7.33 (t, J=7.5 Hz, 1H), 7.25-7.16 (m, 3H), 7.00 (s, 1H), 5.50 (bd s, NH), 4.10-3.95 (m, 1H), 1.25-1.21 (m, 9H). HRMS calcd for C$_{24}$H$_{23}$F$_2$N$_4$O$_2$ (M+H)$^+$ 437.1789; found 437.1795.

[2-Cyclopropylamino-7-(2-fluoro-phenyl)-7H-pyrrolo[2,3-d]pyrimidin-6-yl]-(4-fluoro-phenyl)-methanone: $^1$H NMR (300 MHz, CDCl$_3$) δ 8.80 (s, 1H), 7.99-7.94 (m, 2H), 7.63-7.60 (m, 1H), 7.44-7.6.99 (m, 6H), 5.65 (br s, 1H), 2.87 (s, 1H), 0.80 (s, 2H), 0.57 (s, 2H); HRMS calcd for C$_{22}$H$_{16}$F$_2$N$_4$O (M+H)$^+$ 391.1370; found 391.1387.

(2-Chloro-phenyl)-[7-(4-fluoro-phenyl)-2-(2-methoxy-1-methyl-ethylamino)-7H-pyrrolo[2,3-d]pyrimidin-6-yl]-methanone: $^1$H NMR (300 MHz, CDCl$_3$) δ 8.67 (s, 1H), 7.50-7.34 (m, 6H), 7.19 (t, J=8.3 Hz, 2H), 6.84 (s, 1H), 5.70 (brS, 1H), 4.22 (br s, 1H), 3.39 (s, 3H), 2.37 (t, J=6.8 Hz, 3H); HRMS calcd for C$_{23}$H$_{20}$ClFN$_4$O$_2$ (M+H)$^+$ 439.1337; found 439.1326.

(S)-(4-Fluoro-phenyl)-7-(4-fluoro-phenyl)-2-(2-hydroxy-1,2-dimethyl-propylamino)-7H-pyrrolo[2,3-d]pyrimidin-6-yl]-methanone: $^1$H NMR (300 MHz, CDCl$_3$) δ 8.72 (s, 1H), 7.36 (dd, J=9.0, 5.1 Hz, 2H), 7.25-7.16 (m, 6H), 7.02 (s, 1H), 5.55 (bd s, NH), 4.05 (m, 1H), 2.75 (s, 9H). HRMS calcd for C$_{24}$H$_{23}$F$_2$N$_4$O$_2$ (M+H)$^+$ 437.1789; found 437.1797.

(S)-(2-Chloro-phenyl)-[7-(4-fluoro-phenyl)-2-(2-hydroxy-1,2-dimethyl-propylamino)-7H-pyrrolo[2,3-d]pyrimidin-6-yl]-methanone: $^1$H NMR (300 MHz, CDCl$_3$) δ 8.65 (s, 1H), 7.51-7.37 (m, 5H), 7.24-7.16 (m, 3H), 6.85 (s, 1H), 4.05 (m, 1H), 1.25 (d, J=8.2 Hz, 3H), 1.21 (s, 6H). HRMS calcd for C$_{24}$H$_{22}$ClFN$_4$O$_2$ (M+H)$^+$ 453.1494; found 453.1500.

(S)-[2-sec-Butylamino-7-(4-fluoro-phenyl)-7H-pyrrolo[2,3-d]pyrimidin-6-yl]-(2-chloro-phenyl)-methanone: $^1$H NMR (300 MHz, CDCl$_3$) δ 8.66 (s, 1H), 7.49-7.36 (m, 6H), 7.20 (t, J=7.8 Hz, 2H), 6.83 (s, 1H), 5.35 (bd s, NH), 3.98

(m, 1H), 1.56 (dddd, J=13.6, 8.8, 8.8, 8.8 Hz, 2H), 1.19 (d, J=8.8 Hz, 3H), 0.94 (t, J=7.5 Hz, 3H). HRMS calcd for $C_{24}H_{21}ClFN_4O_2$ (M+H)$^+$ 423.1388; found 423.1371.

(2,4-Dimethyl-phenyl)-[7-(4-fluoro-phenyl)-2-(2-hydroxy-1,2-dimethylpropylamino)-7H-pyrrolo[2,3-d]pyrimidin-6-yl]-methanone: $^1$H NMR (300 MHz, CDCl$_3$) δ 8.65 (s, 1H), 7.49 (d, J=8.3 Hz, 1H), 7.42-7.36 (m, 2H), 7.19 (t, d=8.4 Hz, 2H), 7.12-7.06 (m, 2H), 6.82 (s, 1H), 5.49 (br s, 1H), 4.03 (br s, 1H), 2.39 (d, J=7.7 Hz, 6H), 1.25-1.20 (m, 9H); HRMS calcd for $C_{26}H_{28}FN_4O_2$ (M+H)$^+$ 447.2216; found 447.2196.

(S)-(2-Chloro-phenyl)-[7-(2,6-difluoro-phenyl)-2-(2-methoxy-1-methyl-ethylamino)-7H-pyrrolo[2,3-d]pyrimidin-6-yl]-methanone: $^1$H NMR (300 MHz, CDCl$_3$) δ 8.67 (s, 1H), 7.52-7.35 (m, 5H), 7.14-7.07 (m, 2H), 6.89 (s, 1H), 5.70 (bd s, NH), 4.20 (bd s, 1H), 3.47-3.39 (m, 1H), 3.34 (s, 3H), 1.25 (d, J=6.6 Hz, 3H). HRMS calcd for $C_{23}H_{20}ClF_2N_4O_2$ (M+H)$^+$ 457.1243; found 457.1247.

(2-Chloro-phenyl)-[7-(2,6-difluoro-phenyl)-2-urylamino-7H-pyrrolo[2,3-d]pyrimidin-6-yl]-methanone: $^1$H NMR (300 MHz, CDCl$_3$) δ 8.81 (s, 1H), 7.7.49-7.30 (m, 9H), 6.95 (s, 2H), 2.88 (s, 1H); HRMS calcd for $C_{20}H_{13}F_2N_6O_2$ (M+H)$^+$ 443.0834, found 443.0824.

The compounds which comprise Category II of the present invention have the formula:

the first aspect of which relates to 2-[substituted or unsubstituted]alkylamino-6-[substituted or unsubstituted]aryl-7-[substituted or unsubstituted]aryl pyrrolo[2,3-d]pyrimidines methanone oximes having the formula:

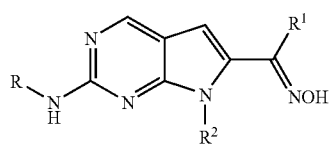

wherein R, R$^1$, and R$^2$ are defined herein below in Table IV.

TABLE IV

| No. | R | R$^1$ | R$^2$ |
|---|---|---|---|
| 121 | 2-methyl-2-hydroxy-1-(S)-methylpropyl | 4-fluorophenyl | 4-fluorophenyl |
| 122 | 2-methyl-2-hydroxy-1-(S)-methylpropyl | 4-fluorophenyl | 2,6-difluorophenyl |
| 123 | 2-methoxy-1-(S)-methylethyl | 4-fluorophenyl | 4-fluorophenyl |
| 124 | 2-methoxy-1-(S)-methylethyl | 4-fluorophenyl | 2,6-difluorophenyl |
| 125 | 2-methyl-2-cyano-1-(S)-methylpropyl | 4-fluorophenyl | 4-fluorophenyl |
| 126 | 2-methyl-2-cyano-1-(S)-methylpropyl | 4-fluorophenyl | 2,6-difluorophenyl |
| 127 | 1-(S)-methylpropyl | 4-fluorophenyl | 4-fluorophenyl |
| 128 | 1-(S)-methylpropyl | 4-fluorophenyl | 2,6-difluorophenyl |
| 129 | N,N-dimethylamino | 4-fluorophenyl | 4-fluorophenyl |
| 130 | N,N-dimethylamino | 4-fluorophenyl | 2,6-difluorophenyl |

TABLE IV-continued

| No. | R | R$^1$ | R$^2$ |
|---|---|---|---|
| 131 | 2-methyl-2-hydroxy-1-(S)-methylpropyl | 2-chlorophenyl | 4-fluorophenyl |
| 132 | 2-methyl-2-hydroxy-1-(S)-methylpropyl | 2-chlorophenyl | 2,6-difluorophenyl |
| 133 | 2-methoxy-1-(S)-methylethyl | 2-chlorophenyl | 4-fluorophenyl |
| 134 | 2-methoxy-1-(S)-methylethyl | 2-chlorophenyl | 2,6-difluorophenyl |
| 135 | 2-methyl-2-cyano-1-(S)-methylpropyl | 2-chlorophenyl | 4-fluorophenyl |
| 136 | 2-methyl-2-cyano-1-(S)-methylpropyl | 2-chlorophenyl | 2,6-difluorophenyl |
| 137 | 1-(S)-methylpropyl | 2-chlorophenyl | 4-fluorophenyl |
| 138 | 1-(S)-methylpropyl | 2-chlorophenyl | 2,6-difluorophenyl |
| 139 | N,N-dimethylamino | 2-chlorophenyl | 4-fluorophenyl |
| 140 | N,N-dimethylamino | 2-chlorophenyl | 2,6-difluorophenyl |
| 141 | 2-methyl-2-hydroxy-1-(S)-methylpropyl | 4-fluorophenyl | 4-fluorophenyl |
| 142 | 2-methyl-2-hydroxy-1-(S)-methylpropyl | 4-fluorophenyl | 2,6-difluorophenyl |
| 143 | 2-methoxy-1-(S)-methylethyl | 4-fluorophenyl | 4-fluorophenyl |
| 144 | 2-methoxy-1-(S)-methylethyl | 4-fluorophenyl | 2,6-difluorophenyl |
| 145 | 2-methyl-2-cyano-1-(S)-methylpropyl | 4-fluorophenyl | 4-fluorophenyl |
| 146 | 2-methyl-2-cyano-1-(S)-methylpropyl | 4-fluorophenyl | 2,6-difluorophenyl |
| 147 | 1-(S)-methylpropyl | 4-fluorophenyl | 4-fluorophenyl |
| 148 | 1-(S)-methylpropyl | 4-fluorophenyl | 2,6-difluorophenyl |
| 149 | N,N-dimethylamino | 4-fluorophenyl | 4-fluorophenyl |
| 150 | N,N-dimethylamino | 4-fluorophenyl | 2,6-difluorophenyl |
| 151 | 2-methyl-2-hydroxy-1-(S)-methylpropyl | 2,6-difluorophenyl | 4-fluorophenyl |
| 152 | 2-methyl-2-hydroxy-1-(S)-methylpropyl | 2,6-di fluorophenyl | 2,6-difluorophenyl |
| 153 | 2-methoxy-1-(S)-methylethyl | 2,6-difluorophenyl | 4-fluorophenyl |
| 154 | 2-methoxy-1-(S)-methylethyl | 2,6-difluorophenyl | 2,6-difluorophenyl |
| 155 | 2-methyl-2-cyano-1-(S)-methylpropyl | 2,6-difluorophenyl | 4-fluorophenyl |
| 156 | 2-methyl-2-cyano-1-(S)-methylpropyl | 2,6-difluorophenyl | 2,6-difluorophenyl |
| 157 | 1-(S)-methylpropyl | 2,6-difluorophenyl | 4-fluorophenyl |
| 158 | 1-(S)-methylpropyl | 2,6-difluorophenyl | 2,6-difluorophenyl |
| 159 | N,N-dimethylamino | 2,6-difluorophenyl | 4-fluorophenyl |
| 160 | N,N-dimethylamino | 2,6-difluorophenyl | 2,6-difluorophenyl |

The compounds which comprise the first aspect of Category II can be prepared beginning with intermediates prepared according to Scheme I, for example, compound 6 depicted in Scheme II herein below.

Scheme II

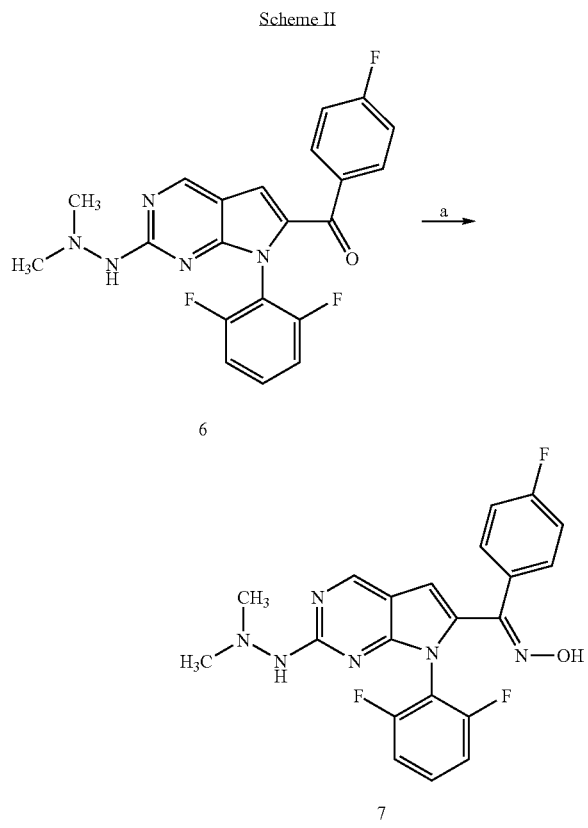

Reagents and conditions: (a) NH₂OH HCl, pyridine; 60° C., 18 hr.

EXAMPLE 2

[7-(2,6-Difluorophenyl)-2-(dimethylamin-1-ylamino)-7H-pyrrolo[2,3-d]pyrimidin-6-yl]-(4-fluorophenyl)-methanone-oxime (7)

Intermediate compound N,N-dimethyl-N'-[7-(2,6-difluoro-phenyl)-7H-pyrrolo[2,3-d]pyrimidin-6-yl]-2-hydrazino-(4-fluoro-phenyl)-methanone, 6, used for the preparation of the following analog, can be prepared according to the procedure outlined herein above in Scheme I.

Preparation of [7-(2,6-difluoro-phenyl)-2-(dimethylamin-1-ylamino)-7H-pyrrolo[2,3-d]pyrimidin-6-yl]-(4-fluorophenyl)-methanone-oxime (7): To a solution of N,N-dimethyl-A-[7-(2,6-difluorophenyl)-7H-pyrrolo[2,3-d]pyrimidin-6-yl]-2-hydrazino-(4-fluoro-phenyl)-methanone, 6, (0.50 g, 1.22 mmol) in pyridine (2 mL) is added hydroxylamine hydrochloride (0.85 g, 12.20 mmol) and the mixture heated to 60° C. overnight. The reaction is then cooled to room temperature and concentrated in vacuo. The crude product is dissolved in EtOAc and washed with H₂O, brine, dried (MgSO₄), filtered and re-concentrated in vacuo to give a yellow solid which is re-crystallized from EtOAc/hexanes to afford 506 mg of the desired product as a yellow powder: $^1$H NMR (300 MHz, CDCl₃) δ 8.37 (s, 1H), 7.22-7.17 (m, 3H), 7.08 (t, J=8.8 Hz, 2H), 6.95 (dd, J=8.4, 8.0 Hz, 1H), 6.32 (d, J=13.2 Hz, 1H), 6.00 (s, 1H), 3.81 (m, 1H), 1.12-1.08 (m, 9H); HRMS calcd for $C_{21}H_{18}F_3N_6O$ (M+H)⁺ 427.1494, found 427.1496.

[7-(2,6-Difluorophenyl)-2-(2-hydroxy-1,2-dimethyl-propylamino)-7H-pyrrolo[2,3-d]pyrimidin-6-yl]-(4-fluorophenyl)-methanone oxime: $^1$H NMR (300 MHz, CDCl₃) δ 8.52 (d, J=7.5 Hz, 1H), 7.49-6.80 (m, 8H), 6.46 (s, 1H), 5.74 (br s, 1H), 3.95 (br s, 1H), 1.30-1.18 (m, 9H); HRMS calcd for $C_{24}H_{22}F_3N_5O_2$ (M+H)⁺ 470.1804, found 470.1823.

(2-Chlorophenyl)-[7-(2,6-difluorophenyl)-2-(2-hydroxy-1,2-dimethyl-propylamino)-7H-pyrrolo[2,3-d]pyrimidin-6-yl]-methanone oxime: $^1$H NMR (300 MHz, CDCl₃) δ 8.70 (br s, 1H), 8.42 (s, 1H), 7.55-7.25 (m, 5H), 7.02 (t, J=7.1 Hz, 2H), 6.25 (s, 1H), 5.26 (d, J=7.1 Hz, 1H), 4.14 (dd, J=9.1, 7.1 Hz, 3H), 3.93 (t=7.1 Hz, 1H), 1.21-1.15 (m, 9H); HRMS calcd for $C_{24}H_{24}F_2N_5O_2$ (M+H)⁺ 452.1898, found 452.1902.

(2-Chlorophenyl)-[7-(2,6-difluorophenyl)-2-(2-hydroxy-1,2-dimethyl-propylamino)-7H-pyrrolo[2,3-d]pyrimidin-6-yl]-methanone oxime: $^1$H NMR (300 MHz, CDCl₃) δ 8.70 (br s, 1H), 8.42 (s, 1H), 7.55-7.25 (m, 5H), 7.02 (t, J=7.1 Hz, 2H), 6.25 (s, 1H), 5.26 (d, J=7.1 Hz, 1H), 4.14 (dd, J=9.1, 7.1 Hz, 3H), 3.93 (t=7.1 Hz, 1H), 1.21-1.15 (m, 9H); HRMS calcd for $C_{24}H_{22}ClF_2N_5O_2$ (M+H)⁺ 486.1508, found 486.1514.

Another iteration of this aspect relates to O-methyl oximes having the formula:

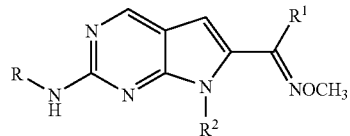

which can be prepared by the following procedure.

Preparation of [7-(2,6-Difluorophenyl)-2-(dimethylamin-1-ylamino)-7H-pyrrolo[2,3-d]pyrimidin-6-yl]-(4-fluorophenyl)-methanone O-methyl-oxime: To a solution of [7-(2,6-difluoro-phenyl)-2-(dimethyl-1-ylamino)-7H-pyrrolo[2,3-d]pyrimidin-6-yl]-(4-fluoro-phenyl)-methanone (0.478 g, 1.04 mmol) in 1-methyl-2-pyrrolidinone (3 mL) is added 1,1-dimethylhydrazine (0.158 mL, 2.08 mmol) and the mixture was heated at 90° C. overnight. The reaction is cooled to room temperature diluted with ethyl acetate and washed with sodium bicarbonate solution, brine, dried over magnesium sulfate, filtered and concentrated in vacuo to afford a brown oil which is purified over silica (hexane:ethyl acetate (6:4), then with ethyl acetate) to afford 100 mg (23% yield) of a yellow solid: $^1$H NMR (300 MHz, CDCl₃) δ 8.37 (s, 1H), 7.44-7.36 (m, 2H), 7.22-7.17 (m, 3H), 7.08 (t, J=8.8 Hz, 2H), 6.95 (dd, J=8.4, 8.0 Hz, 1H), 6.32 (d, J=13.2 Hz, 1H), 6.00 (s, 1H), 3.81 (m, 1H), 1.12-1.08 (m, 9H); HRMS calcd for $C_{22}H_{20}F_3N_6O$ (M+H)⁺ 441.1651, found 441.1650.

The following are further non-limiting examples of this iteration.

[7-(2,6-Difluorophenyl)-2-(2-hydroxy-1,2-dimethyl-propylamino)-7H-pyrrolo[2,3-d]pyrimidin-6-yl]-(4-fluorophenyl)-methanone O-methyl-oxime: $^1$H NMR (300 MHz, CDCl₃) δ 8.53 (d, J=7.5 Hz, 1H), 7.65-6.90 (m 8H), 5.44 (br s, 1H), 4.00 (d, J=6.4 Hz, 1H), 3.54 (s, 3H), 1.30-1.18 (m, 9H); HRMS calcd for $C_{25}H_{24}F_3N_5O_2$ (M+H)⁺ 484.1960, found 484.1943.

(2-Chlorophenyl)-[7-(2,6-difluorophenyl)-2-(2-hydroxy-1,2-dimethyl-propylamino)-7H-pyrrolo[2,3-d]pyrimidin-6-yl]-methanone O-methyl-oxime: $^1$H NMR (300 MHz, CDCl₃) δ 8.46 (s, 1H), 7.51-7.32 (m, 5H), 7.12-7.04 (m, 2H), 6.20 (s, 1H), 5.22-5.20 (m, 1H), 3.97 (s, 1H), 3.53 (s, 3H), 1.23-1.18 (m, 9H); HRMS calcd for $C_{25}H_{24}ClF_2N_5O_2$ (M+H)$^+$ 500.1665, found 500.1667.

[7-(2,6-Difluorophenyl)-2-(piperidin-1-ylamino)-7H-pyrrolo[2,3-d]pyrimidin-6-yl]-(4-fluorophenyl)-methanone O-methyl-oxime: $^1$H NMR (300 MHz, CDCl$_3$) δ 8.37 (s, 1H), 7.44-7.36 (m, 2H), 7.22-7.17 (m, 3H), 7.08 (t, J=8.8 Hz, 2H), 6.95 (dd, J=8.4, 8.0 Hz, 1H), 6.32 (d, J=13.2 Hz, 1H), 6.00 (s, 1H), 3.81 (m, 1H), 1.12-1.08 (m, 9H); HRMS calcd for $C_{25}H_{24}F_3N_6O$ (M+H)$^+$ 481.1964, found 481.1957.

A further aspect of Category II according to the present invention wherein L$^1$ units are —CHOH— units can be prepared from intermediates, such as compound 8, by the procedure described herein below and outlined in Scheme III.

Scheme III

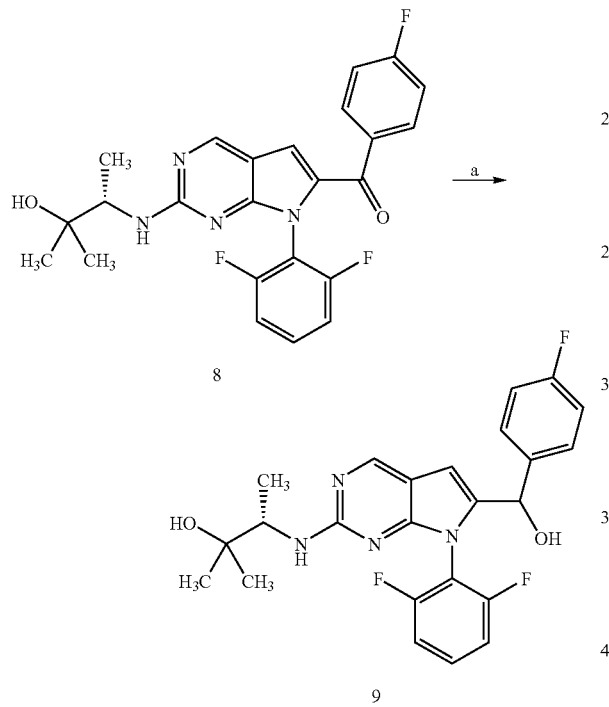

Reagents and conditions: (a) NaBH$_4$, EtOH; rt, 18 hr.

EXAMPLE 3

3-[6-[(2-Chlorophenyl)-hydroxy-methyl]-7-(2,6-difluorophenyl)-7H-pyrrolo[2,3-d]pyrimidin-2-ylamino]-2-methyl-butan-2-ol (9)

Intermediate compound (S)-(2-chloro-phenyl)-[7-(2,6-difluoro-phenyl)-2-(2-hydroxy-1,2-dimethyl-propylamino)-7H-pyrrolo[2,3-d]pyrimidin-6-yl]-methanone, 8, used for the preparation of the following analog, can be prepared according to the procedure outlined herein above in Scheme I.

Preparation of 3-[6-[(2-chlorophenyl)-hydroxy-methyl]-7-(2,6-difluorophenyl)-7H-pyrrolo[2,3-d]pyrimidin-2-ylamino]-2-methyl-butan-2-ol (9): To a solution of (S)-(2-chloro-phenyl)-[7-(2,6-difluoro-phenyl)-2-(2-hydroxy-1,2-dimethyl-propylamino)-7H-pyrrolo[2,3-d]pyrimidin-6-yl]-methanone, 8, (1.0 g, 2.1 mmol) in ethanol (2.4 mL) is added sodium borohydride (0.3 g, 8.5 mmol) and the mixture stirred overnight at room temperature. Aqueous ammonium chloride solution is then added and the mixture is extracted with EtOAc several times and the organic phases combined washed with water, brine, dried (MgSO$_4$), filtered and concentrated in vacuo. The resulting residue is purified over silica (50% EtOAc/hexanes, then 100% EtOAc) to afford 470 mg of the desired product as a yellow solid: $^1$H NMR (300 MHz, CDCl$_3$) δ 8.37 (s, 1H), 7.44-7.36 (m, 2H), 7.22-7.17 (m, 3H), 7.08 (t, J=8.8 Hz, 2H), 6.95 (dd, J=8.4, 8.0 Hz, 1H), 6.32 (d, J=13.2 Hz, 1H), 6.00 (s, 1H), 3.81 (m, 1H), 1.12-1.08 (m, 9H); HRMS calcd for $C_{24}H_{23}ClF_2N_4O_2$ (M+H)$^+$ 473.1556, found 473.1542.

The following are non-limiting examples of this aspect of Category III.

(2-Chlorophenyl)-[7-(2,6-difluorophenyl)-2-(morpholin-4-ylamino)-7H-pyrrolo[2,3-d]pyrimidin-6-yl]-methanol: $^1$H NMR (300 MHz, CDCl$_3$) δ 8.66 (s, 1H), 7.57-7.40 (m, 2H), 7.33-7.20 (m, 3H), 7.15-6.98 (m, 2H), 6.32 (s, 1H), 6.13 (s, 1H), 5.80 (s, 1H), 3.86 (s, 4H), 2.88 (s, 4H); HRMS calcd for $C_{23}H_{20}ClF_2N_5O_2$ (M+H)$^+$ 472.1352, found 472.1343.

An iteration of this aspect relates to O-acyl, inter alia, O-acetyl analogs, for example, wherein L$^1$ is —CHOC(O)CH$_3$, having the formula:

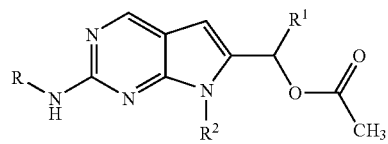

which can be prepared by the procedure described herein below and outlined in Scheme IV.

Scheme IV

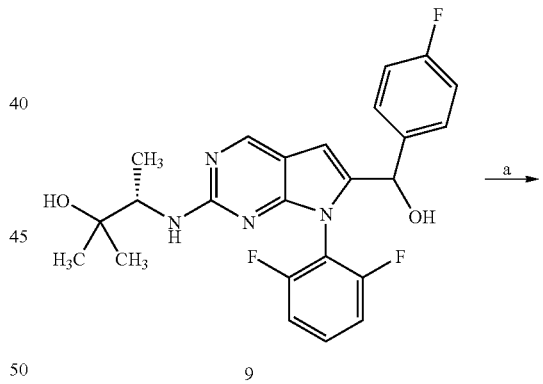

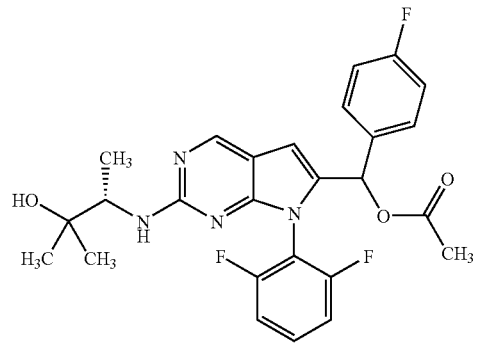

EXAMPLE 4

Preparation of acetic acid (2-chlorophenyl)-[7-(2,6-difluoro-phenyl)-2-(2-hydroxy-1,2-dimethyl-propylamino)-7H-pyrrolo[2,3-d]pyrimidin-6-yl]methylester (10): To a solution of 3-[6-[(2-chloro-phenyl)-hydroxy-methyl]-7-(2,6-difluoro-phenyl)-7H-pyrrolo[2,3-d]pyrimidin-2-ylamino]-2-methyl-butan-2-ol, 9, (0.47 g, 1.00 mmol) and triethylamine (0.60 ml, 4.0 mmol), in pyridine (5 ml) is added dropwise acetyl chloride (0.08 ml, 2.20 mmol). The reaction mixture is stirred under argon at room temperature for 48 hours. Ethyl acetate is added to the mixture and the resulting mixture is washed with water, brine, dried (MgSO$_4$), filtered and concentrated in vacuo. The resulting residue is purified over silica (40% EtOAc/hexanes) to afford 30 mg of the desired: $^1$H NMR (300 MHz, CDCl$_3$) δ 8.42 (s, 1H), 7.52-7.10 (m, 7H), 6.11 (d, J=5.3 Hz, 1H), 4.00-3.91 (m, 1H), 1.97 (d, J=5.9 Hz, 3H), 1.50 (br s, 1H), 1.23 (s, 3H), 1,19 (s, 3H); HRMS calcd for C$_{26}$H$_{25}$ClF$_2$N$_4$O$_3$ (M+H)$^+$ 515.1662, found 515.1644.

A non-limiting example of this iteration includes:

3 {7-(2-Fluoro-phenyl)-6-[(4-fluorophenyl)-hydroxy-methyl]-7H-pyrrolo[pyrimidin-2-ylamino}-2-methyl-butan-2-ol: $^1$H NMR (300 MHz, CDCl$_3$) δ 8.42 (s, 1H), 7.30-6.92 (m, 8H), 6.40 (dd, J=4.0, 3.7 Hz, 1H), 5.72 (d, J=5.5 Hz, 1H), 5.22 (br s, 1H), 3.92 (dd, J=14.6, 7.3 Hz, 1H), 1.22-1.16 (m, 9H); HRMS calcd for C$_{24}$H$_{24}$F$_2$N$_4$O$_2$ (M+H)$^+$ 439.1946, found 439.1960.

The third aspect of Category II relates to L$^1$ units wherein R$^{3a}$ and R$^{3b}$ or R$^{4a}$ and R$^{4b}$ can be taken together to form a ring comprising from 3 to 7 atoms, for example, the cyclic ketals having the formula:

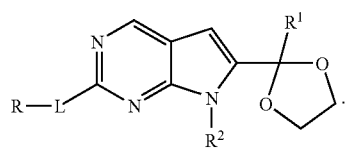

Compounds which comprise this aspect can be prepared beginning with intermediates such as compound 8, as described here below and depicted in Scheme V.

Scheme IV

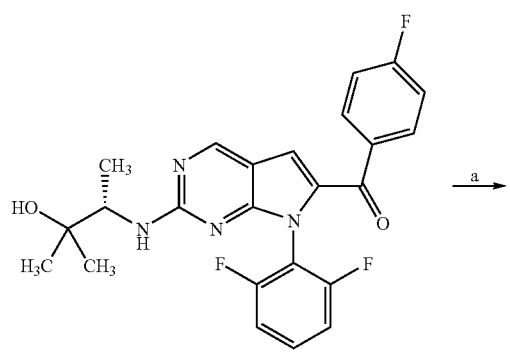

8

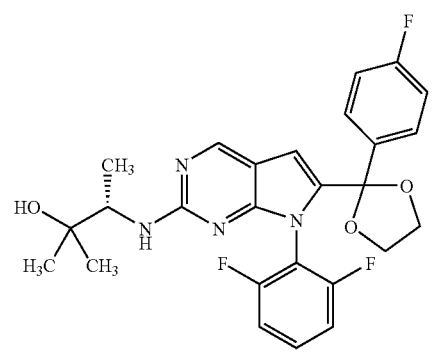

11

EXAMPLE 5

Preparation of 3-{7-(2,6-difluorophenyl)-6-[2-(4-fluorophenyl)-[1,3]dioxolan-2-yl]-7H-pyrrolo[2,3-d]pyrimidin-2-ylamino}-2-methyl-butan-2-ol (10): To a solution of (S)-(2-chlorophenyl)-[7-(2,6-difluorophenyl)-2-(2-hydroxy-1,2-dimethyl-propylamino)-7H-pyrrolo[2,3-d]pyrimidin-6-yl]-methanone, 8, (0.17 g, 0.36 mmol) and ethylene glycol (0.045 ml, 0.726 mmol) in CH$_2$Cl$_2$ (2 ml) is added borane trifluoride etherate (0.02 ml, 0.15 mmol) and the mixture is stirred for 17 hours at room temperature. Additional borane trifluoride etherate (0.01 ml) is added as needed to drive the reaction to completion. The reaction mixture is diluted with H$_2$O and extracted with EtOAc the combined organic phases are washed with additional H$_2$O, aqueous NH$_4$Cl solution, dried (MgSO$_4$), filtered and concentrated in vacuo. The residue is purified over silica (50% EtOAc/hexanes, then 80% EtOAc/hexanes) to afford 68 mg of the desired product as a yellow solid: $^1$H NMR (300 MHz, CDCl$_3$) δ 8.48 (s, 1H), 7.43-6.92 (m, 7H), 6.47 (s, 1H), 8.0 Hz, 1H), 3.98-3.84 (m, 6H), 1.22-1.15 (m, 9H); HRMS calcd for C$_{26}$H$_{25}$F$_3$N$_4$O$_3$ (M+H)$^+$ 499.1957, found 499.1946.

The fourth aspect of Category II relates to L$^1$ units wherein R$^{3a}$ and R$^{3b}$ or R$^{4a}$ and R$^{4b}$ are be taken together to form a unit having the formula =CH[C(R$^6$)$_2$]$_x$CO$_2$R$^6$, for example, compounds having the formula:

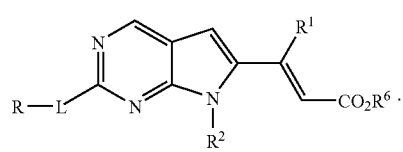

The compound of this aspect of Category II can be prepared by the procedure described herein below and outlined in Scheme VI.

Scheme VI

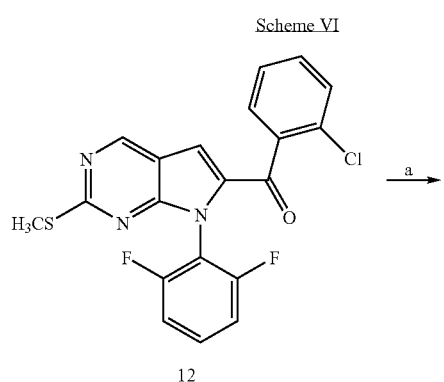

12

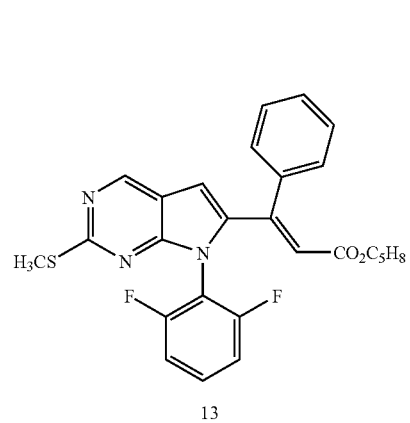

13

Reagents and conditions: (a) (C₂H₅O)₂P(O)CH₂CO₂C₂H₅, NaH, THF; rt, 2 hr.

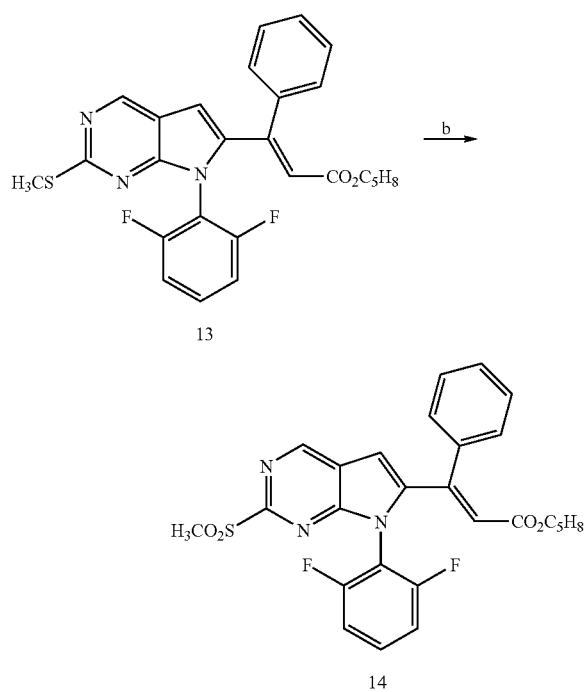

Reagents and conditions: (b) Oxone, H₂O, THF, MeOH; rt, 1 hr.

-continued

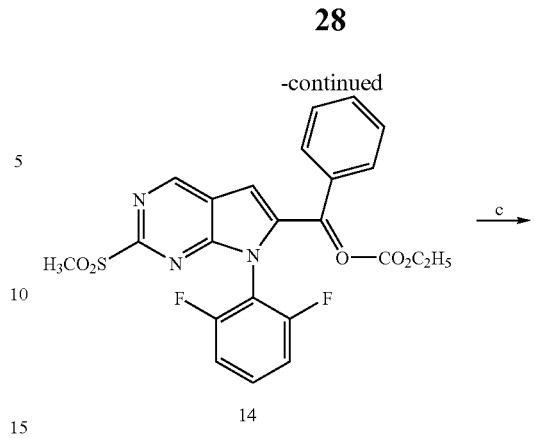

14

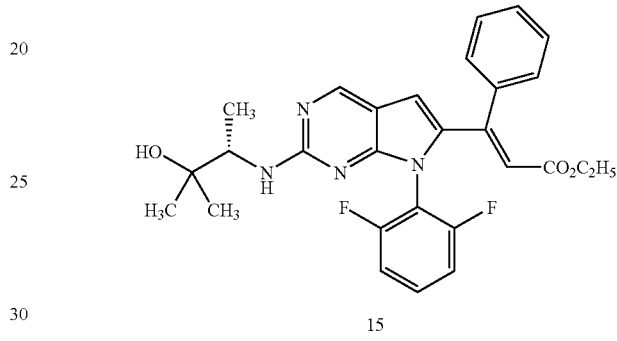

15

Reagents and conditions: (c)

EXAMPLE 6

3-(2-Chlorophenyl)-3-[7-(2,6-difluorophenyl)-2-(2-hydroxy-1,2-dimethyl-propylamino)-7H-pyrrolo[2,3-d]pyrimidin-6-yl]-acrylic acid ethyl ester (15)

Preparation of 3-(2-chlorophenyl)-3-[7-(2,6-difluorophenyl)-2-methylsulfanyl-7H-pyrrolo[2,3-d]pyrimidin-6-yl]-acrylic acid ethyl ester (13): To a suspension of sodium hydride (0.08 g of 60% dispersion in mineral oil, 1.26 mmol) in THF (3 mL) is added triethylphosphonoacetate (0.25 mL, 1.26 mmol) dropwise. After stirring the mixture at room temperature for 5 minutes, a solution of 3-(2-chlorophenyl)-[7-(2,6-difluorophenyl)-2-methylsulfanyl-7H-pyrrolo[2,3-d]pyrimidin-6-yl]-methanone, 12, (0.50 g, 1.20 mmol) in THF (4 mL) is added dropwise. After stirring the mixture at room temp for 2 hours, the reaction mixture is heated to reflux for 2 days. The mixture is dissolved in CHCl₃ and washed with aqueous saturated NH₄Cl solution, dried (MgSO₄), filtered, and concentrated in vacuo. The crude residue is purified over silica (25% EtOAc/hexanes) to afford 390 mg of the desired product: ¹H NMR (300 MHz, CDCl₃) δ 8.79 (s, 1H), 7.45-7.10 (m, 5H), 7.08-6.97 (m, 1H), 6.35 (s, 1H), 6.20 (s, 1H), 4.00 (q, J=6.9 Hz, 2H), 2.45 (s, 3H), 1.05 (t, J=6.9 Hz, 3H); ESI⁺ MS: m/z (rel intensity) 485.9 (100, M⁺+H).

Preparation of 3-(2-chlorophenyl)-3-[7-(2,6-difluorophenyl)-2-methanesulfonyl-7H-pyrrolo[2,3-d]pyrimidin-6-yl]-acrylic acid ethyl ester (14): To a solution of 3-(2-chlorophenyl)-3-[7-(2,6-difluorophenyl)-2-methylsulfanyl-7H-pyrrolo[2,3-d]pyrimidin-6-yl]-acrylic acid ethyl ester, 13, (0.33 g, 0.68 mmol) in THF/methanol (4 mL of 1:1 mixture) is added dropwise a solution of Oxone® (potassium peroxymonosulfate) (1.46 g, 2.38 mmol) in $H_2O$ (4 mL). After stirring the reaction for 1 hour at room temperature, the solution is poured into aqueous saturated $NaHCO_3$. The aqueous phase is extracted with $CHCl_3$ and the combined organic phases are dried ($MgSO_4$), filtered and concentrated in vacuo to afford 0.31 g of the desired product which is used without further purification.

Preparation of 3-(2-chlorophenyl)-3-[7-(2,6-difluorophenyl)-2-(hydroxy-1,2-dimethyl-propylamino)-7H-pyrrolo[2,3-d]pyrimidin-6-yl]-acrylic acid ethyl ester (15): To a solution of 3-(2-chloro-phenyl)-3-[7-(2,6-difluoro-phenyl)-2-methanesulfonyl-7H-pyrrolo[2,3-d]pyrimidin-6-yl]-acrylic acid ethyl ester, 14, (0.30 g, 0.59 mmol)) in N-methylpyrrolidinone (4 mL) is added diisopropylethylamine (0.41 mL, 2.36 mmol) and 3-amino-2-methyl-butan-2-ol hydrochloride salt (0.10 g, 0.71 mmol). After heating the reaction at 90° C. for 21 hours, an additional equivalent of 3-amino-2-methyl-butan-2-ol hydrochloride salt (0.08 g, 0.59 mmol) is added and the mixture heated at 120° C. for 4 hours. The reaction is cooled to room temp and then diluted with aqueous saturated $NH_4Cl$ solution. The aqueous phase is twice extracted with $CHCl_3$ and the organic phase is then washed with aqueous saturated $NaHCO_3$ solution. The organic phase is dried ($MgSO_4$), filtered, concentrated in vacuo and the resulting residue is purified by preparative HPLC to afford the desired product as a yellowish solid: $^1H$ NMR (300 MHz, $d_3$-DMSO) δ 8.64 (s, 1H), 7.64-7.52 (m, 1H), 7.38-7.24 (m, 5H), 7.14-7.08 (m, 1H), 6.57 (s, 1H), 5.95 (s, 1H), 4.31 (bd s, NH), 3.85 (q, J=7.2 Hz, 2H), 3.34 (m, 1H), 1.04 (s, 9H), 0.93 (t, J=7.2 Hz); ESI$^+$ MS: m/z (rel intensity) 541.0 (100, M$^+$+H).

The compounds which comprise Category III of the present invention relate to 2-amino-6-[substituted or unsubstituted]acyl-7-[substituted or unsubstituted]heteroaryl or heterocyclic pyrrolo[2,3-d]pyrimidines having the formula:

wherein R, R$^1$, and R$^2$ are defined herein below in Table V.

TABLE V

| No. | R | R$^1$ | R$^2$ |
|---|---|---|---|
| 161 | 2-hydroxy-1,2-dimethylpropyl | 4-fluorophenyl | 2,5-dimethyl-2H-pyrazol-3-yl |
| 162 | 2-methoxy-1-methylethyl | 4-fluorophenyl | 2,5-dimethyl-2H-pyrazol-3-yl |
| 163 | 1-methylpropyl | 4-fluorophenyl | 2,5-dimethyl-2H-pyrazol-3-yl |
| 164 | N,N-dimethylamino | 4-fluorophenyl | 2,5-dimethyl-2H-pyrazol-3-yl |
| 165 | 2-cyano-1,2-dimethylpropyl | 4-fluorophenyl | 2,5-dimethyl-2H-pyrazol-3-yl |
| 166 | 2-hydroxy-1,2-dimethylpropyl | 4-fluorophenyl | 1H-imidazol-2-yl |
| 167 | 2-methoxy-1-methylethyl | 4-fluorophenyl | 1H-imidazol-2-yl |
| 168 | 1-methylpropyl | 4-fluorophenyl | 1H-imidazol-2-yl |
| 169 | N,N-dimethylamino | 4-fluorophenyl | 1H-imidazol-2-yl |
| 170 | 2-cyano-1,2-dimethylpropyl | 4-fluorophenyl | 1H-imidazol-2-yl |
| 171 | 2-hydroxy-1,2-dimethylpropyl | 4-fluorophenyl | 1H-imidazol-4-yl |
| 172 | 2-methoxy-1-methylethyl | 4-fluorophenyl | 1H-imidazol-4-yl |
| 173 | 1-methylpropyl | 4-fluorophenyl | 1H-imidazol-4-yl |
| 174 | N,N-dimethylamino | 4-fluorophenyl | 1H-imidazol-4-yl |
| 175 | 2-cyano-1,2-dimethylpropyl | 4-fluorophenyl | 1H-imidazol-4-yl |
| 176 | 2-hydroxy-1,2-dimethylpropyl | 4-fluorophenyl | pyridin-4-yl |
| 177 | 2-methoxy-1-methylethyl | 4-fluorophenyl | pyridin-4-yl |
| 178 | 1-methylpropyl | 4-fluorophenyl | pyridin-4-yl |
| 179 | N,N-dimethylamino | 4-fluorophenyl | pyridin-4-yl |
| 180 | 2-cyano-1,2-dimethylpropyl | 4-fluorophenyl | pyridin-4-yl |
| 181 | 2-hydroxy-1,2-dimethylpropyl | 2-chlorophenyl | pyridin-3-yl |
| 182 | 2-methoxy-1-methylethyl | 2-chlorophenyl | pyridin-3-yl |
| 183 | 1-methylpropyl | 2-chlorophenyl | pyridin-3-yl |
| 184 | N,N-dimethylamino | 2-chlorophenyl | pyridin-3-yl |
| 185 | 2-cyano-1,2-dimethylpropyl | 2-chlorophenyl | pyridin-3-yl |
| 186 | 2-hydroxy-1,2-dimethylpropyl | 2-chlorophenyl | pyridin-2-yl |
| 187 | 2-methoxy-1-methylethyl | 2-chlorophenyl | pyridin-2-yl |
| 188 | 1-methylpropyl | 2-chlorophenyl | pyridin-2-yl |
| 189 | N,N-dimethylamino | 2-chlorophenyl | pyridin-2-yl |
| 190 | 2-cyano-1,2-dimethylpropyl | 2-chlorophenyl | pyridin-2-yl |
| 191 | 2-hydroxy-1,2-dimethylpropyl | 2-chlorophenyl | 2,5-dimethyl-2H-pyrazol-3-yl |
| 192 | 2-methoxy-1-methylethyl | 2-chlorophenyl | 2,5-dimethyl-2H-pyrazol-3-yl |
| 193 | 1-methylpropyl | 2-chlorophenyl | 2,5-dimethyl-2H-pyrazol-3-yl |
| 194 | N,N-dimethylamino | 2-chlorophenyl | 2,5-dimethyl-2H-pyrazol-3-yl |
| 195 | 2-cyano-1,2-dimethylpropyl | 2-chlorophenyl | 2,5-dimethyl-2H-pyrazol-3-yl |
| 196 | 2-hydroxy-1,2-dimethylpropyl | 2-chlorophenyl | 1H-imidazol-2-yl |
| 197 | 2-methoxy-1-methylethyl | 2-chlorophenyl | 1H-imidazol-2-yl |
| 198 | 1-methylpropyl | 2-chlorophenyl | 1H-imidazol-2-yl |
| 199 | N,N-dimethylamino | 2-chlorophenyl | 1H-imidazol-2-yl |
| 200 | 2-cyano-1,2-dimethylpropyl | 2-chlorophenyl | 1H-imidazol-2-yl |
| 201 | 2-hydroxy-1,2-dimethylpropyl | 2-chlorophenyl | 1H-imidazol-4-yl |
| 202 | 2-methoxy-1-methylethyl | 2-chlorophenyl | 1H-imidazol-4-yl |
| 203 | 1-methylpropyl | 2-chlorophenyl | 1H-imidazol-4-yl |
| 204 | N,N-dimethylamino | 2-chlorophenyl | 1H-imidazol-4-yl |
| 205 | 2-cyano-1,2-dimethylpropyl | 2-chlorophenyl | 1H-imidazol-4-yl |
| 206 | 2-hydroxy-1,2-dimethylpropyl | 2-chlorophenyl | pyridin-4-yl |
| 207 | 2-methoxy-1-methylethyl | 2-chlorophenyl | pyridin-4-yl |
| 208 | 1-methylpropyl | 2-chlorophenyl | pyridin-4-yl |
| 209 | N,N-dimethylamino | 2-chlorophenyl | pyridin-4-yl |
| 210 | 2-cyano-1,2-dimethylpropyl | 2-chlorophenyl | pyridin-4-yl |

The compounds which comprise the first aspect of Category III can be prepared by the process described herein below and outlined in Scheme VII.

Scheme VII

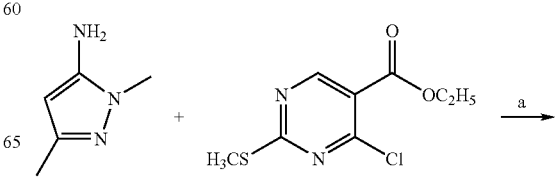

-continued
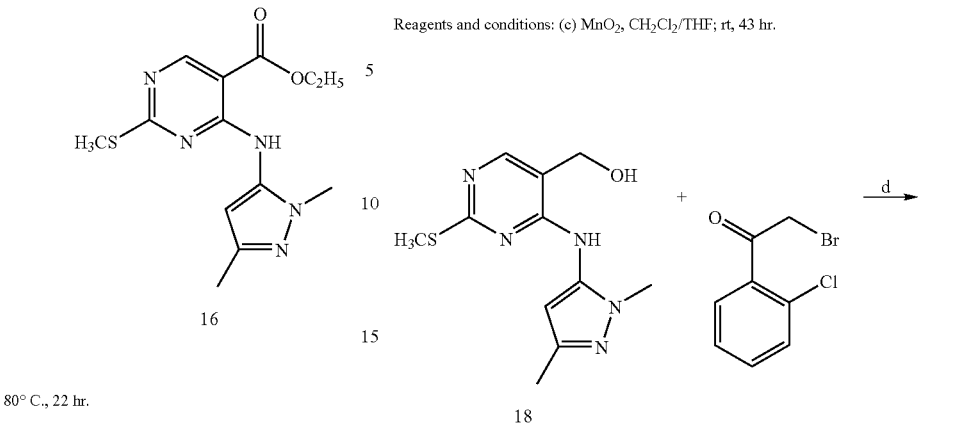
16
Reagents and conditions: (a) EtOH; 80° C., 22 hr.
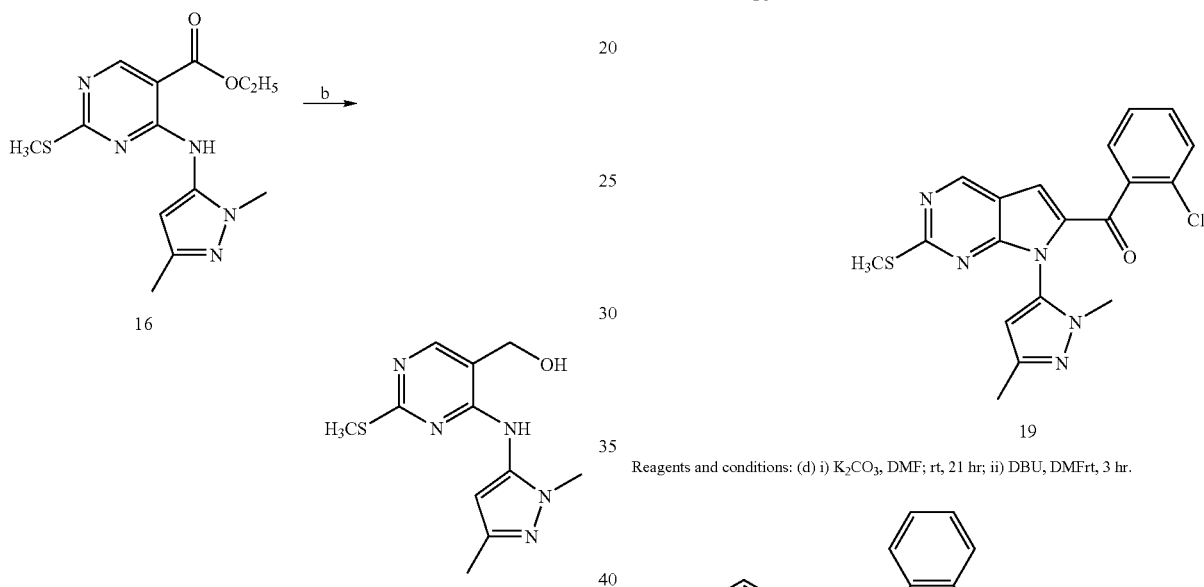
Reagents and conditions: (b) LAH, THF; 0° C. to rt, 1 hr.
17
18
-continued
Reagents and conditions: (c) MnO₂, CH₂Cl₂/THF; rt, 43 hr.
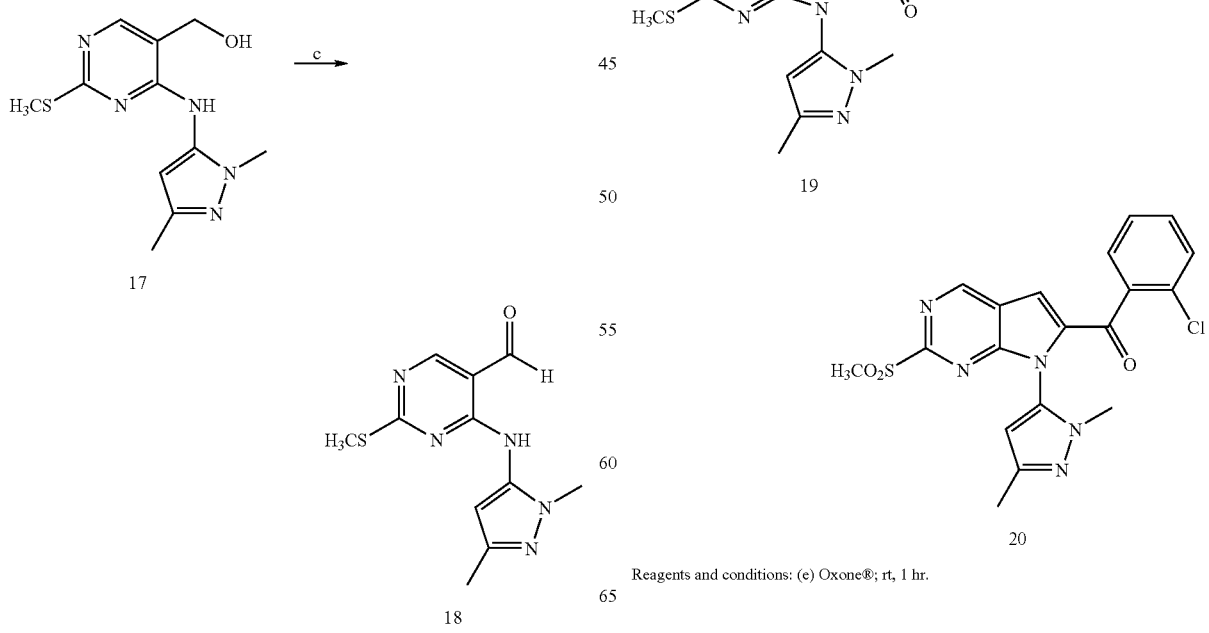
Reagents and conditions: (d) i) K₂CO₃, DMF; rt, 21 hr; ii) DBU, DMF rt, 3 hr.
Reagents and conditions: (e) Oxone®; rt, 1 hr.

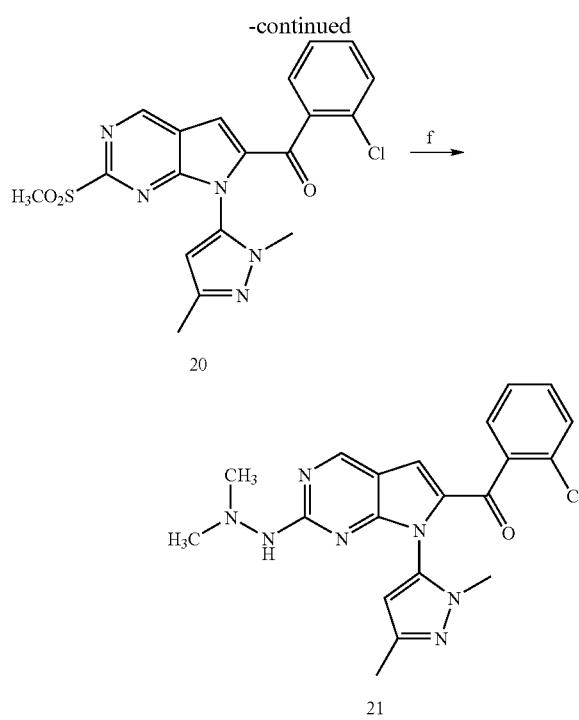

Reagents and conditions: (f) (H₃C)₂NNH₂; NMP; 90° C., 2 hr.

EXAMPLE 7

(2-Chlorophenyl)-[7-(2,5-dimethyl-2H-pyrazol-3-yl)-2-methanesulfonyl-7H-pyrrolo[2,3-d]pyrimidin-6-yl]-methanone (21)

Preparation of 4-(2,5-dimethyl-2H-pyrazol-3-ylamino)-2-methylsulfanyl-pyrimidine-5-carboxylic acid ethyl ester (16): To a solution of 4-chloro-2-methylsulfanyl-pyrimidine-5-carboxylic acid ethyl ester (4.6 g, 19.6 mmol) in ethanol (90 mL) is added 5-amino-1,3-dimethylpyrazole (4.4 g, 39.2 mmol). The mixture is heated for 22 hours at 80° C. The reaction is cooled to room temp and concentrated in vacuo. The solid which remains is dissolved in CHCl₃ and washed with aqueous saturated NaHCO₃ solution. The organic phase is dried (MgSO₄), filtered and concentrated in vacuo and the resulting residue is purified over silica (50% EtOAc//hexanes, followed by 100% EtOAc) to afford 4.8 g of the desired product: ¹H NMR (300 MHz, CDCl₃) δ10.29 (s, NH), 8.82 (s, 1H), 6.30 (s, 1H), 4.43 (q, J=7.2 Hz, 2H), 3.77 (s, 3H), 2.53 (s, 3H), 2.30 (s, 3H), 1.45 (t, J=7.2 Hz, 3H); ESI⁺ MS: m/z (rel intensity) 308.0 (100, M⁺+H).

Preparation of [4-(2,5-dimethyl-2H-pyrazol-3-ylamino)-2-methylsulfanyl-pyrimidin-5-yl]-methanol (17): To a cold (0° C.) solution of 4-(2,5-dimethyl-2H-pyrazol-3-ylamino)-2-methylsulfanyl-pyrimidine-5-carboxylic acid ethyl ester, 16, (2.0 g, 6.5 mmol) in THF (30 mL) is added dropwise lithium aluminum hydride (10.4 mL of IM solution in THF, 10.4 mmol). The reaction is stirred at 0° C. for 5 minutes, then the ice bath is removed and the mixture allowed to stir for 45 minutes at room temperature. The reaction is re-cooled to 0° C., and H₂O (0.4 mL) added dropwise to the mixture. After stirring 10 min at 0° C., NaOH solution (0.4 mL of 2N solution) is added dropwise. After stirring an additional 10 min at 0° C., H₂O (1.2 mL) is added to the mixture, and the mixture stirred at room temperature for 15 minutes. The resulting mixture dried (MgSO₄), filtered and concentrated in vacuo. The resulting residue is purified over silica (5% MeOH//chloroform) to afford 1.0 g of the desired product: ¹H NMR (300 MHz, CDCl₃) δ 8.22 (s, NH), 7.89 (s, 1H), 6.22 (s, 1H), 4.72 (s, 2H), 3.68 (s, 3H), 2.47 (s, 3H), 2.26 (s, 3H); ESI⁺ MS: m/z (rel intensity) 266.0 (100, M⁺+H).

Preparation of 4-(2,5-dimethyl-2H-pyrazol-3-ylamino)-2-methylsulfanyl-pyrimidine-5-carbaldehyde (18): To a solution of [4-(2,5-dimethyl-2H-pyrazol-3-ylamino)-2-methylsulfanyl-pyrimidin-5-yl]-methanol, 17, (0.97 g, 3.66 mmol) in CH₂Cl₂/THF (35 mL of 1:1 mixture) is added manganese (IV) oxide (2.54 g, 29.28 mmol). After stirring the suspension at room temperature for 43 hours, the mixture is filtered through celite, and washed with CH₂Cl₂. The filtrate is concentrated in vacuo and the resulting residue is purified over silica (5% MeOH/chloroform) to afford 0.52 g of the desired product: ¹H NMR (300 MHz, CDCl₃) δ 8.22 (s, NH), 10.58 (s, NH), 9,86 (s, 1H), 8.54 (s, 1H), 6.36 (s, 1H), 3.81 (s, 3H), 2.58 (s, 3H), 2.30 (s, 3H); ESI⁺ MS: m/z (rel intensity) 264.0 (100, M⁺+H).

Preparation of (2-chlorophenyl)-[7-(2,5-dimethyl-2H-pyrazol-3-yl)-2-methylsulfanyl-7H-pyrrolo[2,3-d]pyrimidin-6-yl]-methanone (19): To a solution of 4-(2,5-dimethyl-2H-pyrazol-3-ylamino)-2-methylsulfanyl-pyrimidine-5-carbaldehyde, 18, (0.25 g, 0.95 mmol) in DMF (4 mL) is added 2-bromo-1-(2-chloro-phenyl)-ethanone (0.33 g, 1.42 mmol) and potassium carbonate (0.26 g, 1.90 mmol). The reaction mixture is stirred at room temp for 21 hours after which the reaction solution is diluted with EtOAc and washed three times with aqueous saturated NH₄Cl. The organic phase is washed with brine, dried (MgSO₄), filtered, concentrated in vacuo and the resulting residue is dissolved in DMF (6 mL) and 1,8-diazabicyclo[5.4.0]undec-7-ene (0.28 mL, 1.90 mmol) is added to the reaction. After stirring the reaction at room temp for 3 hours, the mixture is diluted with aqueous saturated NH₄Cl solution and extracted with EtOAc. The organic phase is washed with brine, dried (MgSO₄), filtered, concentrated in vacuo, and the resulting residue is purified over silica (33% EtOAc//hexanes) to afford 0.14 g of the desired product: ¹H NMR (300 MHz, CDCl₃) δ 8.92 (s, 1H), 7.52-7.35 (m, 4H), 7.00 (s, 1H), 6.14 (s, 1H), 3.67 (s, 3H), 2.55 (s, 3H), 2.37 (s, 3H); ESI⁺ MS: m/z (rel intensity) 398.0 (100, M⁺+H).

Preparation of (2-chlorophenyl)-[7-(2,5-dimethyl-2H-pyrazol-3-yl)-2-methanesulfonyl-7H-pyrrolo[2,3-d]pyrimidin-6-yl]-methanone (20): To a solution of (2-chloro-phenyl)-[7-(2,5-dimethyl-2H-pyrazol-3-yl)-2-methylsulfanyl-7H-pyrrolo[2,3-d]pyrimidin-6-yl]-methanone, 19, (0.13 g, 0.34 mmol) in THF:methanol (4 mL of 1:1 mixture) is added dropwise a solution of Oxone® (potassium peroxymonosulfate) (0.73 g, 1.19 mmol) in H₂O (4 mL). After stirring the reaction for 1 hour at room temperature, the solution is poured into aqueous saturated NaHCO₃. The aqueous phase is twice extracted with CHCl₃ and the combined organic phases are dried (MgSO₄), filtered and concentrated in vacuo to afford 0.12 g of the desired product which is used without further purification.

Preparation of (2-chlorophenyl)-[7-(2,5-dimethyl-2H-pyrazol-3-yl)-2-(N,N-dimethyl-N'-methyl-hydrazino)-7H-pyrrolo[2,3-d]pyrimidin-6-yl]-methanone (21): To a solution of (2-chloro-phenyl)-[7-(2,5-dimethyl-2H-pyrazol-3-yl)-2-methanesulfonyl-7H-pyrrolo[2,3-d]pyrimidin-6-yl]-methanone, 20, (0.11 g, 0.29 mmol) in 1-methyl-2-pyrrolidinone (1 mL) is added 1,1-dimethylhydrazine (0.05 mL, 0.58 mmol). The reaction mixture is heated to 90° C. for 2 hours. The mixture is diluted with H₂O and extracted with EtOAc. The organic phase is twice washed with brine, dried (MgSO₄), filtered and concentrated in vacuo with the resulting residue purified over silica (5% MeOH//CHCl₃) to afford 67 mg of the desired product: $^1$H NMR (300 MHz, CDCl₃) □8.85 (s, 1H), 7.49-7.36 (m, 4H), 6.90 (s, 1H), 6.14 (s, 1H), 6.03 (s, NH), 3.65 (s, 3H), 2.69 (s, 6H), 2.36 (s, 3H); ESI⁺ MS: m/z (rel intensity) 410.1 (100, M⁺+H).

The following are non-limiting examples of this aspect of Category III.

(2-Chlorophenyl)-[2-(N,N-dimethyl-N'-methylhydrazino)-7-(5-methyl-isoxazol-3-yl)-7H-pyrrolo[2,3-d]pyrimidin-6-yl]-methanone: $^1$H NMR (300 MHz, CDCl₃) δ 8.85 (s, 1H), 7.57-7.36 (m, 4H), 6.91 (s, 1H), 6.37 (s, 1H), 6.25 (bd s, NH), 2.73 (s, 6H), 2.57 (s, 3H); ESI⁺ MS: m/z (rel intensity) 410.1 (100, M⁺+H).

(2-Chlorophenyl)-[2-(2-hydroxy-1,2-dimethyl-propylamino)-7-(5-methyl-isoxazol-3-yl)-7H-pyrrolo[2,3-d]pyrimidin-6-yl]-methanone: $^1$H NMR (300 MHz, CDCl₃) δ 8.66 (s, 1H), 7.55-7.35 (m, 4H), 6.86 (s, 1H), 6.34 (s, 1H), 5.69 (bd s, NH), 4.15-4.05 (m, 1H), 2.66 (s, 3H), 1.29 (s, 3H), 1.24 (s, 6H); ESI⁺ MS: m/z (rel intensity) 440.1 (100, M⁺+H).

The compounds which comprise Category IV of the present invention have the formula:

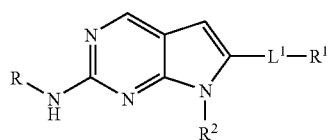

the first aspect of which relates to 2-[substituted or unsubstituted]alkyl, aryl, or heterocyclic amino-7-[substituted or unsubstituted]aryl pyrrolo[2,3-d]pyrimidines-6-carboxylic acid [substituted or unsubstituted]aryl-amides having the formula:

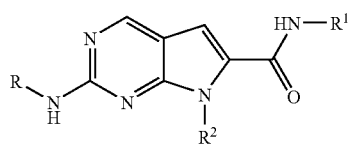

wherein R, R¹, and R² are defined herein below in Table VI

TABLE VI

| No. | R | R¹ | R² |
|---|---|---|---|
| 211 | 2-methyl-2-hydroxy-1-(S)-methylpropyl | 4-fluorophenyl | 4-fluorophenyl |
| 212 | 2-methoxy-1-(S)-methylethyl | 4-fluorophenyl | 4-fluorophenyl |
| 213 | 2-methyl-2-cyano-1-(S)-methylpropyl | 4-fluorophenyl | 4-fluorophenyl |
| 214 | 1-(S)-methylpropyl | 4-fluorophenyl | 4-fluorophenyl |
| 215 | N,N-dimethylamino | 4-fluorophenyl | 4-fluorophenyl |
| 216 | piperidin-1-yl | 4-fluorophenyl | 4-fluorophenyl |
| 217 | morpholin-4-yl | 4-fluorophenyl | 4-fluorophenyl |
| 218 | pyran-4-yl | 4-fluorophenyl | 4-fluorophenyl |
| 219 | phenyl | 4-fluorophenyl | 4-fluorophenyl |
| 220 | 2,6-difluorophenyl | 4-fluorophenyl | 4-fluorophenyl |
| 221 | 2-methyl-2-hydroxy-1-(S)-methylpropyl | 4-fluorophenyl | 2,6-difluorophenyl |
| 222 | 2-methoxy-1-(S)-methylethyl | 4-fluorophenyl | 2,6-difluorophenyl |
| 223 | 2-methyl-2-cyano-1-(S)-methylpropyl | 4-fluorophenyl | 2,6-difluorophenyl |
| 224 | 1-(S)-methylpropyl | 4-fluorophenyl | 2,6-difluorophenyl |
| 225 | N,N-dimethylamino | 4-fluorophenyl | 2,6-difluorophenyl |
| 226 | piperidin-1-yl | 4-fluorophenyl | 2,6-difluorophenyl |
| 227 | morpholin-4-yl | 4-fluorophenyl | 2,6-difluorophenyl |
| 228 | pyran-4-yl | 4-fluorophenyl | 2,6-difluorophenyl |
| 229 | phenyl | 4-fluorophenyl | 2,6-difluorophenyl |
| 230 | 2,6-difluorophenyl | 4-fluorophenyl | 2,6-difluorophenyl |
| 231 | 2-methyl-2-hydroxy-1-(S)-methylpropyl | 2-chlorophenyl | 4-fluorophenyl |
| 232 | 2-methoxy-1-(S)-methylethyl | 2-chlorophenyl | 4-fluorophenyl |
| 233 | 2-methyl-2-cyano-1-(S)-methylpropyl | 2-chlorophenyl | 4-fluorophenyl |
| 234 | 1-(S)-methylpropyl | 2-chlorophenyl | 4-fluorophenyl |
| 235 | N,N-dimethylamino | 2-chlorophenyl | 4-fluorophenyl |
| 236 | piperidin-1-yl | 2-chlorophenyl | 4-fluorophenyl |
| 237 | morpholin-4-yl | 2-chlorophenyl | 4-fluorophenyl |
| 238 | pyran-4-yl | 2-chlorophenyl | 4-fluorophenyl |
| 239 | phenyl | 2-chlorophenyl | 4-fluorophenyl |
| 240 | 2,6-difluorophenyl | 2-chlorophenyl | 4-fluorophenyl |
| 241 | 2-methyl-2-hydroxy-1-(S)-methylpropyl | 2-chlorophenyl | 4-fluorophenyl |
| 242 | 2-methoxy-1-(S)-methylethyl | 2-chlorophenyl | 2,6-difluorophenyl |
| 243 | 2-methyl-2-cyano-1-(S)-methylpropyl | 2-chlorophenyl | 2,6-difluorophenyl |
| 244 | 1-(S)-methylpropyl | 2-chlorophenyl | 2,6-difluorophenyl |
| 245 | N,N-dimethylamino | 2-chlorophenyl | 2,6-difluorophenyl |
| 246 | piperidin-1-yl | 2-chlorophenyl | 2,6-difluorophenyl |
| 247 | morpholin-4-yl | 2-chlorophenyl | 2,6-difluorophenyl |
| 248 | pyran-4-yl | 2-chlorophenyl | 2,6-difluorophenyl |
| 249 | phenyl | 2-chlorophenyl | 2,6-difluorophenyl |
| 250 | 2,6-difluorophenyl | 2-chlorophenyl | 2,6-difluorophenyl |

The compounds which comprise the first aspect of Category IV can be prepared by the procedure described herein below and outline in Scheme VIII.

Scheme VIII

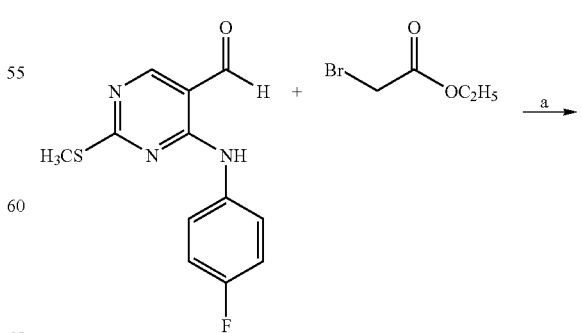

22

37
-continued
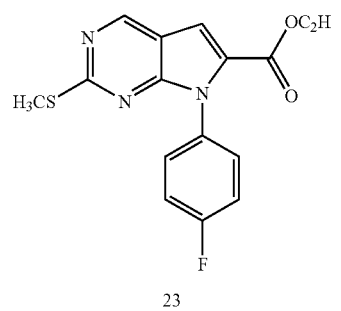
23
Reagents and conditions: (a) K₂CO₃, DMF; rt, 19 hr.
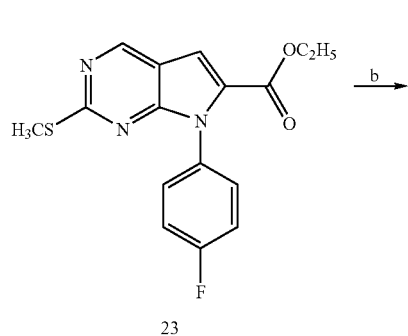
23
Reagents and conditions: (b) NaOH, THF/H₂O; rt, 3 hr.
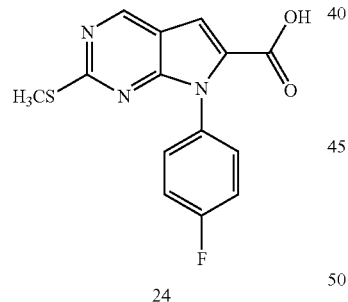
24
38
-continued
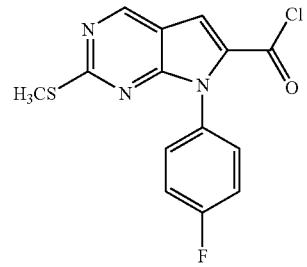
25
Reagents and conditions: (c) oxalyl chloride, CH₂Cl₂; 0° C., to rt, 3 hr.
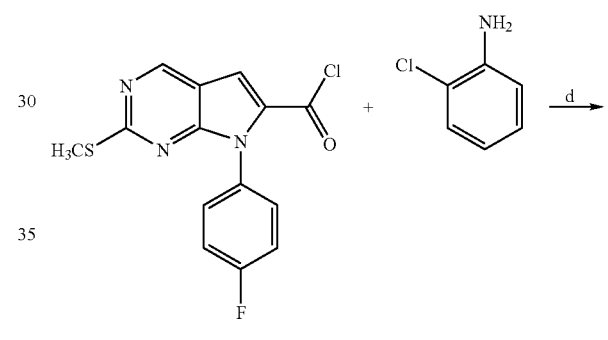
25
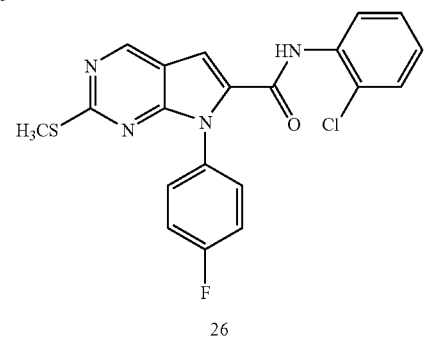
26
Reagents and conditions: (d) TEA, Ch₂Cl₂; rt, 16 hr.
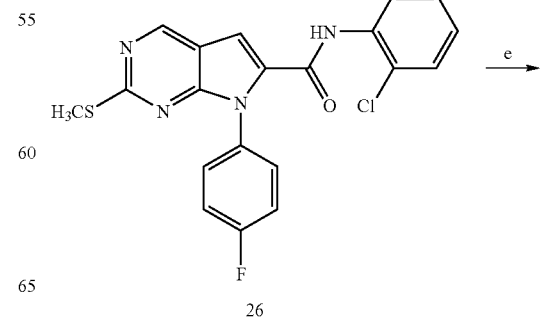
26

-continued

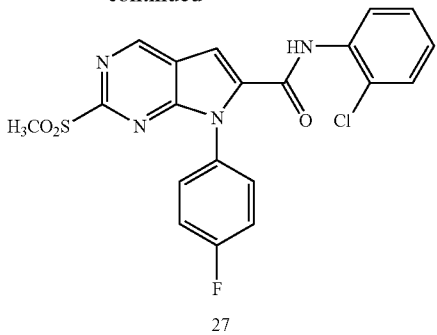

Reagents and conditions: (e) mCPBA, CH₂Cl₂; 0° C. to rt, 2 hr.

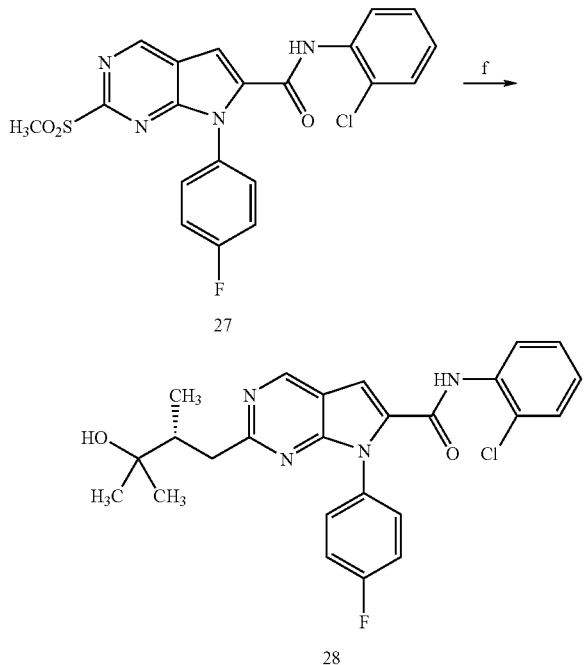

Reagents and conditions: (f) 3-amino-2-methyl-butan-2-ol; NMP; 90° C., 2 hr.

EXAMPLE 8

7-(4-Fluorophenyl)-2-(2-hydroxy-1,2-dimethyl-propylamino)-7H-pyrrolo[2,3-d]pyrimidine-6-carboxylic acid (2-chlorophenyl)-amide (28)

Starting material, intermediate 18, can be prepared in the same manner as intermediate 2, described herein above in Scheme I, by substituting 4-fluoroaniline for 2,6-difluoroaniline.

Preparation of 7-(4-fluorophenyl)-2-methylsulfanyl-7H-pyrrolo[2,3-d]pyrimidine-6-carboxylic acid methyl ester (23): To a solution of 4-(4-fluorophenylamino)-2-methylsulfanyl-pyrimidine-5-carbaldehyde, 22, (26.3 g, 100.0 mmol) in dimethylformamide (450 mL) is added potassium carbonate (41.5 g, 300.2 mmol) and methyl bromoacetate (14.7 mL, 150.0 mmole). The mixture is allowed to stir at ambient temperature for 19 hours. The reaction is then diluted with H₂O and extracted three times with EtOAc. The organic layer is washed with brine, dried (MgSO₄), filtered, and concentrated in vacuo. The resulting residue is purified over silica (10% to 40% EtOAc/hexanes) to afford 6.9 g of the desired product as a yellow solid: $^1$H NMR (300 MHz, CDCl₃) δ 8.94 (s, 1H), 7.42 (s, 1H), 7.36 (dd, J=8.2, 5.9 Hz, 2H), 7.22 (t, J=8.7 Hz, 1H), 3.82 (s, 3H), 2.49 (s, 3H); ESI$^+$ MS: m/z (rel intensity) 317.9 (100, M$^+$+H).

Preparation of 7-(4-fluorophenyl)-2-methylsulfanyl-7H-pyrrolo[2,3-d]pyrimidine-6-carboxylic acid (24): To a solution of 7-(4-fluorophenyl)-2-methylsulfanyl-7H-pyrrolo[2,3-d]pyrimidine-6-carboxylic acid methyl ester, 23, (3.1 g, 9.7 mmol) in THF (40 mL) is added a solution of NaOH (3.9 g, 97.0 mmol) in water (30 mL). The reaction is allowed to stir for 3 hours at room temperature before the mixture is diluted with H₂O and extracted three times with EtOAc. The aqueous phase is acidified slowly to pH 1-2 with conc. HCl and then extracted three times with EtOAc. The combined organic phases are rinsed with brine, dried (MgSO₄), filtered, and concentrated in vacuo to afford 2.5 g of the desired product which was used without further purification: $^1$H NMR (300 MHz, d₆-DMSO) δ 9.06 (s, 1H), 7.44 (s, 1H), 7.52 (dd, J=8.2, 5.9 Hz, 2H), 7.38 (t, J=8.7 Hz, 1H), 2.44 (s, 3H); ESI$^+$ MS: m/z (rel intensity) 304.0 (100, M$^+$+H).

Preparation of 7-(4-fluorophenyl)-2-methylsulfanyl-7H-pyrrolo[2,3-d]pyrimidine-6-carbonyl chloride (25): To a cold (0° C.) solution of 7-(4-fluoro-phenyl)-2-methylsulfanyl-7H-pyrrolo[2,3-d]pyrimidine-6-carboxylic acid, 24, (4.7 g, 15.5 mmol) in dichloromethane (100 mL) is added DMF (0.5 mL) followed by dropwise addition of oxalyl chloride (2.7 mL, 31.1 mmol). The mixture is allowed to slowly warm to room temperature over a period of 3 hours. The reaction mixture is concentrated in vacuo and can be dried azeotropically with toluene to afford 4.7 g of the desired product, which is used without further purification: $^1$H NMR (300 MHz, CDCl₃) δ 9.38 (s, 1H), 8.04 (s, 1H), 7.40-7.20 (m, 4H), 2.58 (s, 3H); ESI$^+$ MS: m/z (rel intensity) 322.0 (100, M$^+$+H).

Preparation of 7-(4-fluorophenyl)-2-methylsulfanyl-7H-pyrrolo[2,3-d]pyrimidine-6-carboxylic acid (2-chlorophenyl)-amide (26): To a solution of 7-(4-fluoro-phenyl)-2-methylsulfanyl-7H-pyrrolo[2,3-d]pyrimidine-6-carbonyl chloride, 25, (0.57 g, 1.77 mmol) in dichloromethane (10 mL) is added 2-chloroaniline (0.28 mL, 2.66 mmol) and triethylamine (0.74 mL, 5.3 mmol). The mixture is allowed to stir at ambient temperature for 16 hours. The reaction was diluted with H₂O and extracted three times with EtOAc. The combined organic phases are rinsed with brine, dried (MgSO₄), filtered and concentrated in vacuo wherein the crude residue is purified over silica (5% to 40% EtOAc/hexanes) to afford 365 mg the desired product: $^1$H NMR (300 MHz, CDCl₃) δ 9.00 (s, 1H), 8.42 (d, J=8.2 Hz, 1H), 8.32 (br s, NH), 7.55-7.50 (m, 2H), 7.42 (d, J=8.2 Hz, 1H), 7.36-7.20 (m, 3H), 7.12 (t, J=8.7 Hz, 1H), 2.49 (s, 3H); ESI$^+$ MS: m/z (rel intensity) 413.0 (100, M$^+$+H).

Preparation of 7-(4-fluorophenyl)-2-methanesulfonyl-7H-pyrrolo[2,3-d]pyrimidine-6-carboxylic acid (2-chlorophenyl)-amide (27): To a cold (0° C.) solution of 7-(4-fluorophenyl)-2-methylsulfanyl-7H-pyrrolo[2,3-d]pyrimidine-6-carboxylic acid (2-chlorophenyl)-amide, 26, (0.37 g, 0.88 mmol) in CH₂Cl₂ (15 mL) is added 3-chloroperoxybenzoic acid (0.64 g of 77% mixture, 2.21 mmol). After allowing the mixture to warm to room temp over a period of 2 hours, the mixture is diluted with EtOAc and washed with saturated NaHCO₃ solution (4×) and brine. The organic phase is dried (MgSO₄), filtered, and concentrated in vacuo to afford 360 mg of the desired product, which is used without further purification: $^1$H NMR (300 MHz, CDCl₃) δ 9.38 (s, 1H), 8.42 (d, J=8.2 Hz, 1H), 8.32 (br s, NH), 7.55-7.50 (m, 2H), 7.42 (d, J=8.2 Hz, 1H), 7.36-7.20 (m, 3H), 7.12 (t, J=8.7 Hz, 1H), 3.38 (s, 3H); ESI⁺ MS: m/z (rel intensity) 445.0 (100, M⁺+H).

Preparation of 7-(4-fluorophenyl)-2-(2-hydroxy-1,2-dimethyl-propylamino)-7H-pyrrolo[2,3-d]pyrimidine-6-carboxylic acid (2-chlorophenyl)-amide (28): To a solution of 7-(4-fluoro-phenyl)-2-methanesulfonyl-7H-pyrrolo[2,3-d]pyrimidine-6-carboxylic acid (2-chloro-phenyl)-amide, 27, (0.11 g, 0.25 mmol) in N-methyl-pyrrolidinone (3 mL) is added diisopropylethylamine (0.22 mL, 1.28 mmol) and 3-amino-2-methyl-butan-2-ol hydrochloride salt (0.11 g, 0.77 mmol). The mixture is heated to 140° C. for 4 hours and the resulting solution purified by preparative HPLC to afford the desired product as a yellowish solid: ¹H NMR (300 MHz, CDCl₃) δ 8.58 (s, 1H), 8.33 (d, J=8.1 Hz, 1H), 8.23 (s, 1H), 7.45-7.40 (m, 3H), 7.32-7.22 (m, 3H), 7.13 (t, J=8.1 Hz, 2H), 3.92-3.82 (m, 1H), 1.26 (d, J=9.1 Hz, 6H), 1.20 (d, J=6.8 Hz, 3H); ESI⁺ MS: m/z (rel intensity) 468.0.0 (100, M⁺+H).

The following are non-limiting examples of compounds according to aspect one of Category IV.

7-(4-Fluorophenyl)-2-phenoxy-7H-pyrrolo[2,3-d]pyrimidine-6-carboxylic acid (2-chlorophenyl)-amide, (xx): ¹H NMR (300 MHz, CDCl₃) δ 8.96 (s, 1H), 8.41 (d, J=8.2 Hz, 1H), 8.27 (s, 1H), 7.50-7.39 (m, 5H), 7.34-7.18 (m, 5H), 7.12 (t, J=8.2 Hz, 2H); ESI⁺ MS: m/z (rel intensity) 458.9 (100, M⁺+H).

2-(2,6-Difluorophenylamino)-7-(4-fluoro-phenyl)-7H-pyrrolo[2,3-d]pyrimidine-6-carboxylic acid (2-chlorophenyl)-amide, (xx): ¹H NMR (300 MHz, CDCl₃) δ 8.84 (s, 1H), 8.41 (d, J=8.5 Hz, 1H), 8.24 (s, 1H), 7.48-7.40 (m, 3H), 7.32-7.16 (m, 4H), 7.10 (t, J=6.0 Hz, 2H); ESI⁺ MS: m/z (rel intensity) 493.9 (100, M⁺+H).

The second aspect of Category IV relates to 2-[substituted or unsubstituted]alkyl, aryl, or heterocyclic amino-7-[substituted or unsubstituted]aryl pyrrolo[2,3-d]pyrimidines-6-[substituted or unsubstituted]aryl-ethanone having the formula:

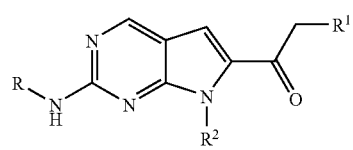

wherein R, R¹, and R² are defined herein below in Table VII

TABLE VII

| No. | R | R¹ | R² |
|---|---|---|---|
| 251 | 2-methyl-2-hydroxy-1-(S)-methylpropyl | 2,6-dichlorophenyl | 4-fluorophenyl |
| 252 | 2-methoxy-1-(S)-methylethyl | 2,6-dichlorophenyl | 4-fluorophenyl |
| 253 | 2-methyl-2-cyano-1-(S)-methylpropyl | 2,6-dichlorophenyl | 4-fluorophenyl |
| 254 | 1-(S)-methylpropyl | 2,6-dichlorophenyl | 4-fluorophenyl |
| 255 | N,N-dimethylamino | 2,6-dichlorophenyl | 4-fluorophenyl |
| 256 | piperidin-1-yl | 2,6-dichlorophenyl | 4-fluorophenyl |
| 257 | morpholin-4-yl | 2,6-dichlorophenyl | 4-fluorophenyl |
| 258 | pyran-4-yl | 2,6-dichlorophenyl | 4-fluorophenyl |
| 259 | phenyl | 2,6-dichlorophenyl | 4-fluorophenyl |
| 260 | 2,6-difluorophenyl | 2,6-dichlorophenyl | 4-fluorophenyl |
| 261 | 2-methyl-2-hydroxy-1-(S)-methylpropyl | 2,6-dichlorophenyl | 2,6-difluorophenyl |
| 262 | 2-methoxy-1-(S)-methylethyl | 2,6-dichlorophenyl | 2,6-difluorophenyl |
| 263 | 2-methyl-2-cyano-1-(S)-methylpropyl | 2,6-dichlorophenyl | 2,6-difluorophenyl |
| 264 | 1-(S)-methylpropyl | 2,6-dichlorophenyl | 2,6-difluorophenyl |
| 265 | N,N-dimethylamino | 2,6-dichlorophenyl | 2,6-difluorophenyl |
| 266 | piperidin-1-yl | 2,6-dichlorophenyl | 2,6-difluorophenyl |
| 267 | morpholin-4-yl | 2,6-dichlorophenyl | 2,6-difluorophenyl |
| 268 | pyran-4-yl | 2,6-dichlorophenyl | 2,6-difluorophenyl |
| 269 | phenyl | 2,6-dichlorophenyl | 2,6-difluorophenyl |
| 270 | 2,6-difluorophenyl | 2,6-dichlorophenyl | 2,6-difluorophenyl |
| 271 | 2-methyl-2-hydroxy-1-(S)-methylpropyl | 2-chlorophenyl | 4-fluorophenyl |
| 272 | 2-methoxy-1-(S)-methylethyl | 2-chlorophenyl | 4-fluorophenyl |
| 273 | 2-methyl-2-cyano-1-(S)-methylpropyl | 2-chlorophenyl | 4-fluorophenyl |
| 274 | 1-(S)-methylpropyl | 2-chlorophenyl | 4-fluorophenyl |
| 275 | N,N-dimethylamino | 2-chlorophenyl | 4-fluorophenyl |
| 276 | piperidin-1-yl | 2-chlorophenyl | 4-fluorophenyl |
| 277 | morpholin-4-yl | 2-chlorophenyl | 4-fluorophenyl |
| 278 | pyran-4-yl | 2-chlorophenyl | 4-fluorophenyl |
| 279 | phenyl | 2-chlorophenyl | 4-fluorophenyl |
| 280 | 2,6-difluorophenyl | 2-chlorophenyl | 4-fluorophenyl |
| 281 | 2-methyl-2-hydroxy-1-(S)-methylpropyl | 2-chlorophenyl | 4-fluorophenyl |
| 282 | 2-methoxy-1-(S)-methylethyl | 2-chlorophenyl | 2,6-difluorophenyl |
| 283 | 2-methyl-2-cyano-1-(S)-methylpropyl | 2-chlorophenyl | 2,6-difluorophenyl |
| 284 | 1-(S)-methylpropyl | 2-chlorophenyl | 2,6-difluorophenyl |
| 285 | N,N-dimethylamino | 2-chlorophenyl | 2,6-difluorophenyl |
| 286 | piperidin-1-yl | 2-chlorophenyl | 2,6-difluorophenyl |
| 287 | morpholin-4-yl | 2-chlorophenyl | 2,6-difluorophenyl |
| 288 | pyran-4-yl | 2-chlorophenyl | 2,6-difluorophenyl |
| 289 | phenyl | 2-chlorophenyl | 2,6-difluorophenyl |
| 290 | 2,6-difluorophenyl | 2-chlorophenyl | 2,6-difluorophenyl |

The compounds which comprise the second aspect of Category IV can be prepared by the procedure described herein below and outline in Scheme IX.

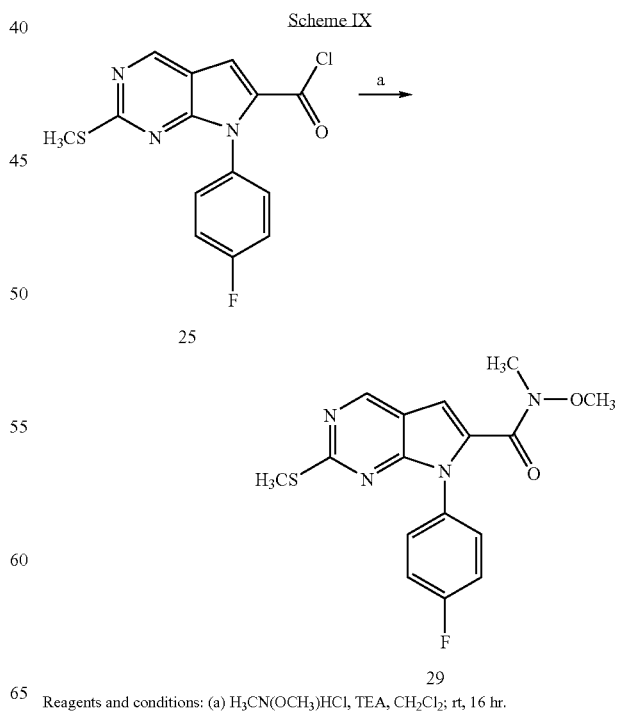

Scheme IX

Reagents and conditions: (a) H₃CN(OCH₃)HCl, TEA, CH₂Cl₂; rt, 16 hr.

-continued

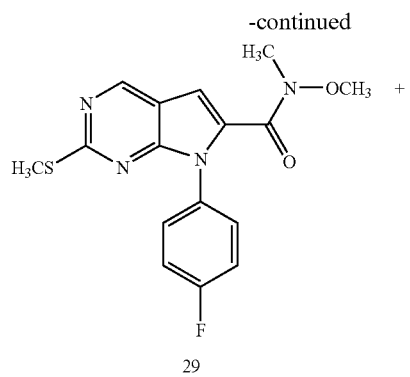

29

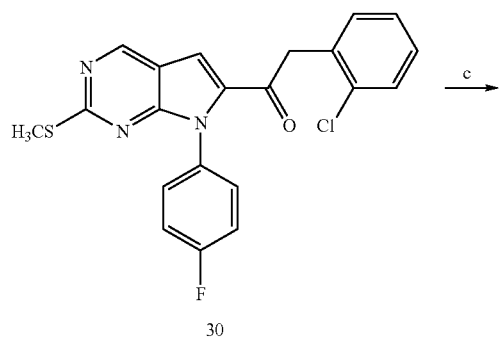

Reagents and conditions: (b) Mg, Et₂O, THF, rt, 2 hr.

30

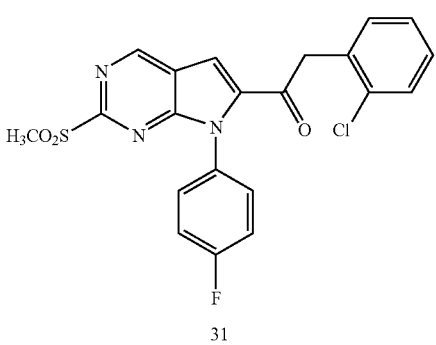

31

Reagents and conditions: (c) mCPBA, CH₂Cl₂; 0° C. to rt, 2 hr.

-continued

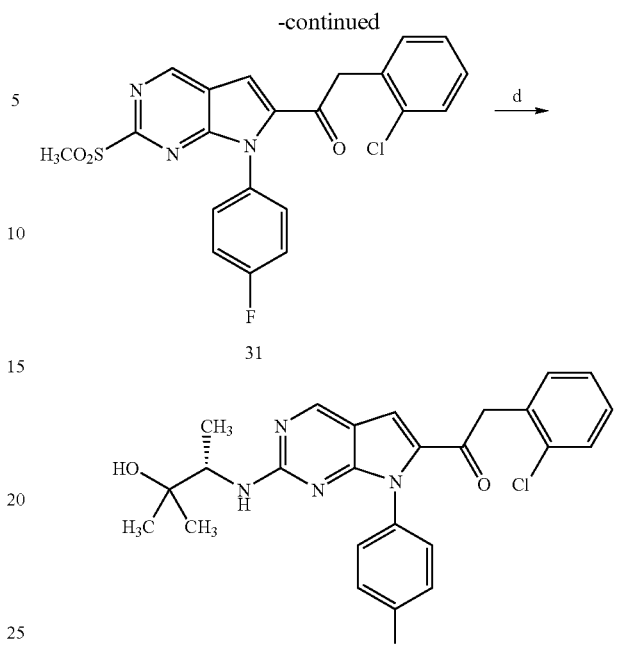

Reagents and conditions: (d) 3-amino-2-methyl-butan-2-ol, DIPEA, NPM; 120° C., 4 hr.

EXAMPLE 9

2-(2-Chlorophenyl)-1-[7-(4-fluorophenyl)-2-(2-hydroxy-1,2-dimethyl-propylamino)-7H-pyrrolo[2,3-d]pyrimidin-6-yl]-ethanone (32)

Preparation of 7-(4-fluorophenyl)-2-methylsulfanyl-7H-pyrrolo[2,3-d]pyrimidine-6-carboxylic acid methoxy-methyl-amide (29): To a solution of 7-(4-fluoro-phenyl)-2-methylsulfanyl-7H-pyrrolo[2,3-d]pyrimidine-6-carbonyl chloride, 25, (1.02 g, 3.15 mmol) in CH₂Cl₂ (20 mL) is added N,O-dimethylhydroxylamine hydrochloride salt (0.37 g, 3.80 mmol) and triethylamine (1.32 mL, 9.50 mmol). The mixture is allowed to stir at room temperature for 16 hours. The reaction is diluted with H₂O and extracted three times with EtOAc and the combined organic layers are washed with brine, dried (MgSO₄), filtered and concentrated in vacuo. The crude residue is purified over silica (5% to 40% EtOAc/hexanes) to afford 660 mg of the desired product: ¹H NMR (300 MHz, CDCl₃) δ 8.90 (s, 1H), 7.44 (dd, J=8.4, 5.9 Hz, 2H), 7.22 (dd, J=8.4, 5.9 Hz, 2H), 7.10 (s, 1H), 3.62 (s, 3H), 3.26 (s, 3H), 2.54 (s, 3H); ESI⁺ MS: m/z (rel intensity) 347.0 (100, M⁺+H).

Preparation of 2-(2-chlorophenyl)-1-[7-(4-fluorophenyl)-2-methylsulfanyl-7H-pyrrolo[2,3-d]pyrimidin-6-yl]-ethanone (30): To a round bottom flask equipped with a condenser is added Mg powder (0.35 g, 0.02 mmol) and diethyl ether (10 mL). 2-Chlorobenzyl bromide (0.10 mL, 0.76 mmol) and a catalytic amount of 1,2-dibromoethane (5 µL) is added to the reaction mixture. After an initial exotherm, the reaction solution develops a yellow color. 7-(4-Fluorophenyl)-2-methylsulfanyl-7H-pyrrolo[2,3-d]pyrimidine-6-carboxylic acid methoxy-methyl-amide, 29, (0.22 g, 0.63 mmol) is dissolved in THF (10 mL) and the Grignard reagent is then carefully transferred dropwise using a cannula using nitrogen to initiate and continue the transfer. The mixture is allowed to stir at room temperature for 2 hours after which the magnesium is removed by filtration and the filtrate concentrated in vacuo. The residue is purified by preparative HPLC to afford 64 mg of the desired product as a pale colored solid: $^1$H NMR (300 MHz, CDCl$_3$) δ 9.02 (s, 1H), 7.60 (s, 1H), 7.42-7.38 (m, 1H), 7.37-7.22 (m, 5H), 7.18 (t, J=8.7 Hz, 2H), 4.40 (s, 2H), 2.44 (s, 3H); ESI$^+$ MS: m/z (rel intensity) 411.9 (100, M$^+$+H).

Preparation of 2-(2-chlorophenyl)-1-[7-(4-fluorophenyl)-2-methanesulfonyl-7H-pyrrolo[2,3-d]pyrimidin-6-yl]-ethanone (31): To a cold (0° C.) solution of 2-(2-chlorophenyl)-1-[7-(4-fluorophenyl)-2-methylsulfanyl-7H-pyrrolo[2,3-d]pyrimidin-6-yl]-ethanone, 30, (0.06 g, 0.15 mmol) in CH$_2$Cl$_2$ (6 mL) is added 3-chloroperoxybenzoic acid (0.07 g of 77% mixture, 0.39 mmol). The mixture is allowed to warm to room temperature over a period of 2 hours. The mixture is diluted with EtOAc, washed with aqueous saturated NaHCO$_3$ solution, brine, and the organic phase is dried (MgSO$_4$), filtered, and concentrated in vacuo to afford 73 mg of the desired product which was used without further purification: $^1$H NMR (300 MHz, CDCl$_3$) δ 9.38 (s, 1H), 8.20 (s, 1H), 7.68 (s, 1H), 7.42-7.38 (m, 1H), 7.37-7.22 (m, 5H), 7.18 (t, J=8.7 Hz, 2H), 4.44 (s, 2H), 3.32 (s, 3H); ESI$^+$ MS: m/z (rel intensity) 443.9 (100, M$^+$+H).

Preparation of 2-(2-chlorophenyl)-1-[7-(4-fluorophenyl)-2-(2-hydroxy-1,2-dimethyl-propylamino)-7H-pyrrolo[2,3-d]pyrimidin-6-yl]-ethanone (32): To a solution of 2-(2-chloro-phenyl)-1-[7-(4-fluorophenyl)-2-methanesulfonyl-7H-pyrrolo[2,3-d]pyrimidin-6-yl]-ethanone, 31, (0.036 g, 0.080 mmol) in N-methylpyrrolidinone (2 mL) is added diisopropylethylamine (0.071 mL, 0.410 mmol) and 3-amino-2-methyl-butan-2-ol hydrochloride salt (0.035 g, 0.240 mmol). The mixture is heated to 120° C. for 4 hours. The reaction crude product is then purified by preparative HPLC to afford the desired product as a yellowish solid: $^1$H NMR (300 MHz, CDCl$_3$) δ 8.60 (s, 1H), 7.54 (s, 1H), 7.42-7.38 (m, 1H), 7.32-7.10 (m, 7H), 4.36 (s, 2H), 3.92-3.82 (m, 1H), 1.26 (d, J=9.1 Hz, 6H), 1.20 (d, J=6.8 Hz, 3H); ESI$^+$ MS: m/z (rel intensity) 467.0 (100, M$^+$+H).

The following are non-limiting examples of compounds according to the second aspect of Category IV.

2-(2-Chlorophenyl)-1-[7-(4-fluorophenyl)-2-(1-phenyl-ethylamino)-7H-pyrrolo[2,3-d]pyrimidin-6-yl]-ethanone:
$^1$H NMR (300 MHz, CDCl$_3$) δ 10.02 (br d, NH), 8.62 (s, 1H), 7.50 (s, 1H), 7.42-7.37 (m, 1H), 7.30-7.14 (m, 10H), 7.13-7.05 (m, 2H), 4.82 (q, br, 1H), 4.30 (s, 2H), 1.60 (d, J=7.0 Hz, 3H); ESI$^+$ MS: m/z (rel intensity) 485.0 (100, M$^+$+H).

The third aspect of Category IV relates to 2-[substituted or unsubstituted]alkyl, aryl, or heterocyclic amino-7-[substituted or unsubstituted]aryl pyrrolo[2,3-d]pyrimidines-6-[substituted or unsubstituted]aryl or alkyl-sulfonyl compounds having the formula:

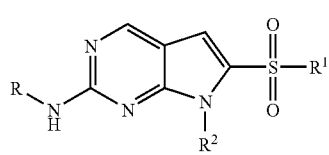

wherein R, R$^1$, and R$^2$ are defined herein below in Table VIII

TABLE VIII

| No. | R | R$^1$ | R$^2$ |
|---|---|---|---|
| 291 | 2-methyl-2-hydroxy-1-(S)-methylpropyl | 2,6-dichlorophenyl | 4-fluorophenyl |
| 292 | 2-methoxy-1-(S)-methylethyl | 2,6-dichlorophenyl | 4-fluorophenyl |
| 293 | 2-methyl-2-cyano-1-(S)-methylpropyl | 2,6-dichlorophenyl | 4-fluorophenyl |
| 294 | 1-(S)-methylpropyl | 2,6-dichlorophenyl | 4-fluorophenyl |
| 295 | N,N-dimethylamino | 2,6-dichlorophenyl | 4-fluorophenyl |
| 296 | piperidin-1-yl | 2,6-dichlorophenyl | 4-fluorophenyl |
| 297 | morpholin-4-yl | 2,6-dichlorophenyl | 4-fluorophenyl |
| 298 | pyran-4-yl | 2,6-dichlorophenyl | 4-fluorophenyl |
| 299 | phenyl | 2,6-dichlorophenyl | 4-fluorophenyl |
| 300 | 2,6-difluorophenyl | 2,6-dichlorophenyl | 4-fluorophenyl |
| 301 | 2-methyl-2-hydroxy-1-(S)-methylpropyl | 2,6-dichlorophenyl | 2,6-difluorophenyl |
| 302 | 2-methoxy-1-(S)-methylethyl | 2,6-dichlorophenyl | 2,6-difluorophenyl |
| 303 | 2-methyl-2-cyano-1-(S)-methylpropyl | 2,6-dichlorophenyl | 2,6-difluorophenyl |
| 304 | 1-(S)-methylpropyl | 2,6-dichlorophenyl | 2,6-difluorophenyl |
| 305 | N,N-dimethylamino | 2,6-dichlorophenyl | 2,6-difluorophenyl |
| 306 | piperidin-1-yl | 2,6-dichlorophenyl | 2,6-difluorophenyl |
| 307 | morpholin-4-yl | 2,6-dichlorophenyl | 2,6-difluorophenyl |
| 308 | pyran-4-yl | 2,6-dichlorophenyl | 2,6-difluorophenyl |
| 309 | phenyl | 2,6-dichlorophenyl | 2,6-difluorophenyl |
| 310 | 2,6-difluorophenyl | 2,6-dichlorophenyl | 2,6-difluorophenyl |
| 311 | 2-methyl-2-hydroxy-1-(S)-methylpropyl | 2-chlorophenyl | 4-fluorophenyl |
| 312 | 2-methoxy-1-(S)-methylethyl | 2-chlorophenyl | 4-fluorophenyl |
| 313 | 2-methyl-2-cyano-1-(S)-methylpropyl | 2-chlorophenyl | 4-fluorophenyl |
| 314 | 1-(S)-methylpropyl | 2-chlorophenyl | 4-fluorophenyl |
| 315 | N,N-dimethylamino | 2-chlorophenyl | 4-fluorophenyl |
| 316 | piperidin-1-yl | 2-chlorophenyl | 4-fluorophenyl |
| 317 | morpholin-4-yl | 2-chlorophenyl | 4-fluorophenyl |
| 318 | pyran-4-yl | 2-chlorophenyl | 4-fluorophenyl |
| 319 | phenyl | 2-chlorophenyl | 4-fluorophenyl |
| 320 | 2,6-difluorophenyl | 2-chlorophenyl | 4-fluorophenyl |
| 321 | 2-methyl-2-hydroxy-1-(S)-methylpropyl | 2-chlorophenyl | 4-fluorophenyl |
| 322 | 2-methoxy-1-(S)-methylethyl | 2-chlorophenyl | 2,6-difluorophenyl |
| 323 | 2-methyl-2-cyano-1-(S)-methylpropyl | 2-chlorophenyl | 2,6-difluorophenyl |
| 324 | 1-(S)-methylpropyl | 2-chlorophenyl | 2,6-difluorophenyl |
| 325 | N,N-dimethylamino | 2-chlorophenyl | 2,6-difluorophenyl |
| 326 | piperidin-1-yl | 2-chlorophenyl | 2,6-difluorophenyl |
| 327 | morpholin-4-yl | 2-chlorophenyl | 2,6-difluorophenyl |
| 328 | pyran-4-yl | 2-chlorophenyl | 2,6-difluorophenyl |
| 329 | phenyl | 2-chlorophenyl | 2,6-difluorophenyl |
| 330 | 2,6-difluorophenyl | 2-chlorophenyl | 2,6-difluorophenyl |

The compounds which comprise the third aspect of Category IV can be prepared by the procedure described herein below and outlined in Scheme X.

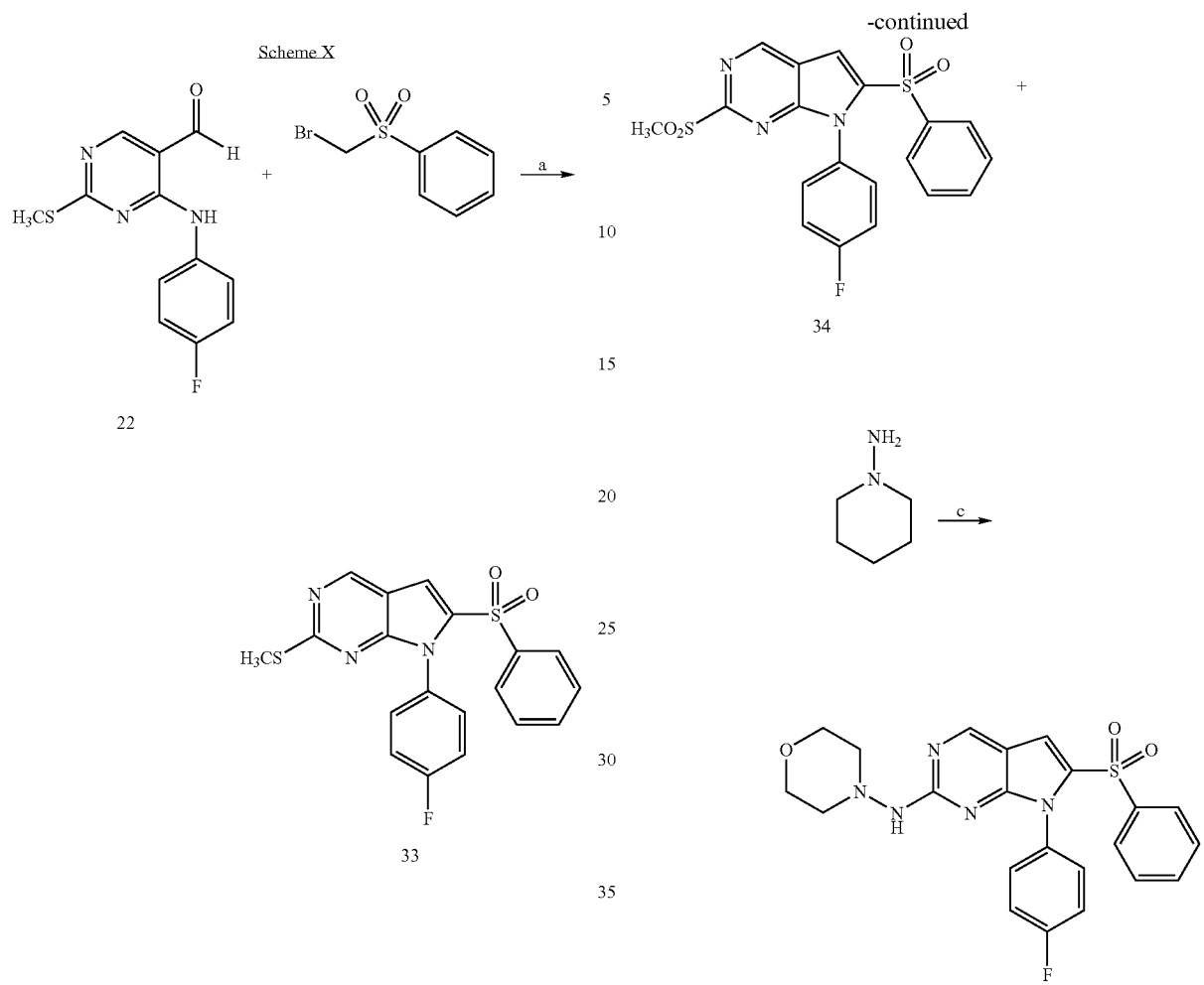
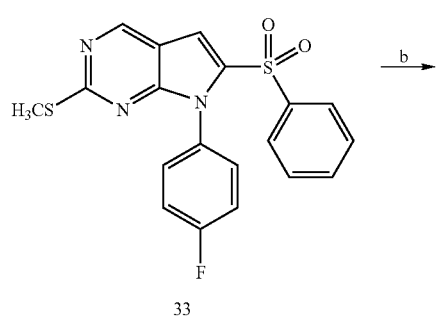

Reagents and conditions: (a) DMF, rt, 19 hr.
Reagents and conditions: (b) mCPBA, CH$_2$Cl$_2$; 0° C. to rt, 2 hr.
Reagents and conditions: (c) DIPEA, NMP; 90° C., 21 hr.

EXAMPLE 10

[6-Benzenesulfonyl-7-(4-fluorophenyl)-7H-pyrrolo[2,3-d]pyrimidin-2-yl]-morpholin-4-yl-amine (35)

Preparation of 6-benzenesulfonyl-7-(4-fluoro-phenyl)-2-methylsulfanyl-7H-pyrrolo[2,3-d]pyrimidine (33): To a solution of 4-(2,6-difluoro-phenylamino)-2-methylsulfanyl-pyrimidine-5-carbaldehyde, 22, (1.18 g, 4.48 mmol) in DMF (20 mL) is added potassium carbonate (1.86 g, 13.4 mmol) and bromomethanesulfonyl benzene (1.58 g, 6.70 mmol). The mixture is stirred at room temperature for 19 hour then diluted with H$_2$O and the resulting mixture is extracted with EtOAc. The combined organic phases are washed with brine, dried (MgSO$_4$), filtered, concentrated in vacuo, and the crude residue is purified over silica (10% to 40% EtOAc/hexanes) to afford 480 g of the desired product as a yellow solid: $^1$H NMR (300 MHz, CDCl$_3$) δ 9.12 (s, 1H), 7.98 (s, 1H), 8.06 (d, J=8.2 Hz, 2H), 7.70 (dd, J=8.8, 5.5 Hz, 2H), 7.58 (d, J=8.2 Hz, 2H), 7.28-7.20 (m, 3H), 2.58 (s, 3H); ESI$^+$ MS: m/z (rel intensity) 399.8 (100, M$^+$+H).

Preparation of 6-benzenesulfonyl-7-(4-fluorophenyl)-2-methanesulfonyl-7H-pyrrolo[2,3-d]pyrimidine (34): To a cold (0° C.) solution of 6-benzenesulfonyl-7-(4-fluoro-phenyl)-2-methylsulfanyl-7H-pyrrolo[2,3-d]pyrimidine, 33, (0.24 g, 0.61 mmol) in $CH_2Cl_2$ (10 mL) is added 3-chloroperoxybenzoic acid (77%, 0.37 g, 1.51 mmol). After stirring the mixture at room temperature for 2 hours, the reaction mixture is diluted with EtOAc and washed with aqueous saturated $NaHCO_3$ solution, brine, dried ($MgSO_4$), filtered, and concentrated in vacuo to afford 192 mg of the desired product: $^1H$ NMR (300 MHz, $CDCl_3$) δ 9.52 (s, 1H), 8.32 (s, 1H), 8.06 (d, J=8.2 Hz, 2H), 7.70-7.64 (m, 2H), 7.62 (d, J=8.7 Hz, 2H), 7.42 (t, J=8.7 Hz, 1H), 7.36 (dd, J=8.8, 5.5 Hz, 2H), 3.38 (s, 3H); $ESI^+$ MS: m/z (rel intensity) 431.8 (100, $M^++H$).

Preparation of [6-Benzenesulfonyl-7-(4-fluorophenyl)-7H-pyrrolo[2,3-d]pyrimidin-2-yl]-morpholin-4-yl-amine (35): 6-Benzenesulfonyl-7-(4-fluoro-phenyl)-2-methanesulfonyl-7H-pyrrolo[2,3-d]pyrimidine, 34, (0.04 g, 0.10 mmol) in N-methylpyrrolidinone (3 mL) is added diisopropylethylamine (0.41 mL, 2.36 mmol) and 3-amino-2-methyl-butan-2-ol hydrochloride salt (0.10 g, 0.71 mmol). The mixture is heated to 90° C. for 21 hours. The product is purified by preparative HPLC to afford 50 mg of the desired product as a yellowish solid: $^1H$ NMR (300 MHz, d6-DMSO) δ 8.64 (s, 1H), 7.64-7.47 (m, 1H), 7.42-7.25 (m, 5H), 7.14-7.09 (m, 1H), 6.56 (s, 1H), 5.95 (s, 1H), 4.30 (s, 1H), 3.85 (q, J=7.2 Hz, 2H), 1.04 (s, 9H), 0.93 (t, J=7.2 Hz, 3H); $ESI^+$ MS: m/z (rel intensity) 540.9 (100, $M^++H$).

Compounds listed and described herein above have been found in many instances to exhibit activities ($IC_{50}$ in the cell based assay described herein below or ones which are referenced herein) at a level below 1 micromolar (μM).

The compounds of the present invention are capable of effectively blocking the production of inflammatory cytokine production from cells, which thereby allows for the mitigation, alleviation, control, abatement, retardation, or prevention of one or more disease states or syndromes which are related to the extracellular release of one or more cytokines.

Inflammatory Disease States

Inflammatory disease states include those which are related to the following non-limiting examples:
  i) Interleukin-1 (IL-1): implicated as the molecule responsible for a large number of disease states, inter alia, rheumatoid arthritis, osteoarthritis, as well as other disease states which relate to connective tissue degradation.
  ii) Cycloxygenase-2 (COX-2): inhibitors of cytokine release are proposed as inhibitors of inducible COX-2 expression, which has been shown to be increased by cytokines. M. K. O'Banion et al., *Proc. Natl. Acad. Sci. U.S.A.*, 89, 4888 (1998).
  iii) Tumor Necrosis Factor-α (TNF-α): This pro-inflammatory cytokine is suggested as an important mediator in many disease states or syndromes, inter alia, rheumatoid arthritis, osteoarthritis, inflammatory bowel disease (IBS), septic shock, cardiopulmonary dysfunction, acute respiratory disease, and cachexia.

Each of the disease states or conditions which the formulator desires to treat may require differing levels or amounts of the compounds described herein to obtain a therapeutic level. The formulator can determine this amount by any of the known testing procedures known to the artisan.

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

FORMULATIONS

The present invention also relates to compositions or formulations which comprise the inflammatory cytokine release-inhibiting compounds according to the present invention. In general, the compositions of the present invention comprise:
  a) an effective amount of one or more 2,6,7-substituted pyrrolo[2,3-d]pyrimidines and derivatives thereof according to the present invention which are effective for inhibiting release of inflammatory cytokines; and
  b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Non-limiting examples of compositions according to the present invention include:
  a) from about 0.001 mg to about 1000 mg of one or more 2,6,7-substituted pyrrolo[2,3-d]pyrimidines according to the present invention; and
  b) one or more excipient.

Another embodiment according to the present invention relates to the following compositions:
  a) from about 0.01 mg to about 100 mg of one or more 2,6,7-substituted pyrrolo[2,3-d]pyrimidines according to the present invention; and
  b) one or more pharmaceutical excipient.

A further embodiment according to the present invention relates to the following compositions:
  a) from about 0.1 mg to about 10 mg of one or more 2,6,7-substituted pyrrolo[2,3-d]pyrimidines according to the present invention; and
  b) one or more pharmaceutical excipient.

The term "effective amount" as used herein means "an amount of one or more 2,6,7-substituted pyrrolo[2,3-d]pyrimidines, effective at dosages and for periods of time necessary to achieve the desired result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present invention can be administered as frequently as necessary to achieve a therapeutic amount.

METHOD OF USE

The present invention also relates to a method for controlling the level of one or more inflammation inducing cytokines, inter alia, interleukin-1 (IL-1), Tumor Necrosis Factor-α (TNF-α), interleukin-6 (IL-6), and interleukin-8 (IL-8) and thereby controlling, mediating, or abating disease states affected by the levels of extracellular inflammatory cytokines. The present method comprises the step of administering to a human or higher mammal an effective amount of a composition comprising one or more of the inflammatory cytokine inhibitors according to the present invention.

The present invention also relates to the use of the 2,6,7-substituted pyrrolo[2,3-d]pyrimidines according to the present invention in the manufacture of a medicament for the treatment of inflammatory cytokine related disorders. These disorders are described herein above under Inflammatory Disease States.

Because the inflammatory cytokine inhibitors of the present invention can be delivered in a manner wherein more than one site of control can be achieved, more than one disease state can be modulated at the same time. Non-limiting examples of diseases which are affected by control or inhibition of inflammatory cytokine inhibitors, thereby modulating excessive cytokine activity, include osteoarthritis, rheumatoid arthritis, diabetes, human Immunodeficiency virus (HIV) infection.

PROCEDURES

The compounds of the present invention can be evaluated for efficacy, for example, measurements of cytokine inhibition constants, $K_i$, and $IC_{50}$ values can be obtained by any method chosen by the formulator.

Non-limiting examples of suitable assays include:
i) UV-visible substrate enzyme assay as described by L. Al Reiter, *Int. J. Peptide Protein Res.*, 43, 87-96 (1994).
ii) Fluorescent substrate enzyme assay as described by Thornberry et al., *Nature*, 356, 768-774 (1992).
iii) PBMC Cell assay as described in U.S. Pat. No. 6,204,261 B1 Batchelor et al., issued Mar. 20, 2001.

Each of the above citations is included herein by reference.

In addition, Tumor Necrosis Factor, TNF-α, inhibition can be measured by utilizing lipopolysaccharide (LPS) stimulated human monocytic cells (THP-1) as described in:
i) K. M. Mohler et al., "Protection Against a Lethal Dose of Endotoxin by an Inhibitor of Tumour Necrosis Factor Processing", *Nature*, 370, pp 218-220 (1994).
ii) U.S. Pat. No. 6,297,381 B1 Cirillo et al., issued Oct. 2, 2001, incorporated by reference and reproduced herein below in relevant portion thereof.

The inhibition of cytokine production can be observed by measuring inhibition of TNF-α in lipopolysaccharide stimulated THP cells. All cells and reagents are diluted in RPMI 1640 with phenol red and L-glutamine, supplemented with additional L-glutamine (total: 4 mM), penicillin and streptomycin (50 units/mL each) and fetal bovine serum (FBS 3%) (GIBCO, all conc. Final). Assay is performed under sterile conditions, only test compound preparation is non-sterile. Initial stock solutions are made in DMSO followed by dilution into RPMI 1640 2-fold higher than the desired final assay concentration. Confluent THP.1 cells ($2 \times 10^6$ cells/mL, final conc.; American Type Culture Company, Rockville, Md.) are added to 96 well polypropylene round bottomed culture plates (Costar 3790; sterile) containing 125 μL test compound (2-fold concentrated) or DMSO vehicle (controls, blanks). DMSO concentration should not exceed 0.2% final. Cell mixture is allowed to preincubate for 30 minutes at 37° C., 5% $CO_2$ prior to stimulation with lipopolysaccharide (LPS, 1 μg/mL final; Sigma L-2630, from *E. coli* serotype 0111.B4; stored as 1 mg/mL stock in endotoxin screened diluted $H_2O$ vehicle at –80° C.). Blanks (unstimulated) receive $H_2O$ vehicle; final incubation volume is 250 μL. Incubation (4 hours) proceeds as described above. Assay is to be terminated by centrifuging plates 5 minutes at room temperature, 1600 rpm (4033 g); supernatants are then transferred to clean 96 well plates and stored at –80° C. until analyzed for human TNF-α by a commercially available ELISA kit (Biosource #KHC3015, Camarillo, Calif.). The calculated $IC_{50}$ value is the concentration of the test compound that caused a 50% decrease in the maximal TNF-α production.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound including all enantiomeric and diasteriomeric forms and pharmaceutically acceptable salts thereof, said compound having the formula:

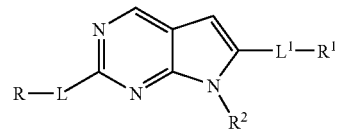

wherein:
R has the formula:

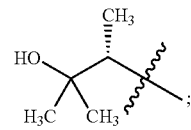

$R^1$ is hydrogen or substituted or unsubstituted $C_6$-$C_{10}$ aryl;
$R^2$ is substituted or unsubstituted $C_6$-$C_{10}$ aryl;
L and $L^1$ are linking units each of which is independently chosen from:
  i) —NH—;
  ii) —O—;
  iii) —$SO_2$—;
  iv) —C(O)—;
  v) —C=$NOR^6$;
  vi) —C($R^6$)$_2$—;
  vii) —C[=C($R^6$)$_2$]—; and
  viii) —C($OR^5$)$_2$—;
$R^5$ is hydrogen, —$COR^6$, or two $R^5$ units can be taken together with the oxygen atoms to form a cyclic ketal ring comprising 5 or 6 atoms; and
$R^6$ is methyl, ethyl, or n-propyl.

2. A composition comprising:
   a) an effective amount of one or more compounds according to claim 1; and
   b) one or more pharmaceutically acceptable excipients.

* * * * *